United States Patent
Cheung et al.

(10) Patent No.: US 10,449,323 B2
(45) Date of Patent: Oct. 22, 2019

(54) HUMIDIFICATION SYSTEM

(71) Applicant: Fisher & Paykel Healthcare Limited, Auckland (NZ)

(72) Inventors: Dexter Chi Lun Cheung, Auckland (NZ); Matthew Jon Payton, Auckland (NZ); Michael Barraclough, Auckland (NZ); Michael John Andresen, Auckland (NZ); Kieran Michael Orchard, Auckland (NZ); Philip James Edgeworth, Auckland (NZ); Peter Kenneth Graham, Auckland (NZ); Anthony James Newland, Auckland (NZ); Daniel John Smith, Auckland (NZ); Timothy James Beresford Sharp, Auckland (NZ); Elmo Benson Stoks, Auckland (NZ); Jonathan Mark Church, Auckland (NZ); Andre van Schalkwyk, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 14/389,331

(22) PCT Filed: Mar. 28, 2013

(86) PCT No.: PCT/NZ2013/000054
§ 371 (c)(1),
(2) Date: Sep. 29, 2014

(87) PCT Pub. No.: WO2013/147623
PCT Pub. Date: Oct. 3, 2013

(65) Prior Publication Data
US 2015/0048530 A1 Feb. 19, 2015

Related U.S. Application Data

(60) Provisional application No. 61/618,573, filed on Mar. 30, 2012, provisional application No. 61/785,644, filed on Mar. 14, 2013.

(51) Int. Cl.
*A61M 16/16* (2006.01)
*A61M 16/08* (2006.01)
(Continued)

(52) U.S. Cl.
CPC ........ *A61M 16/161* (2014.02); *A61M 16/024* (2017.08); *A61M 16/0875* (2013.01);
(Continued)

(58) Field of Classification Search
CPC ............ A61M 16/1075; A61M 16/109; A61M 16/161; A61M 16/024; A61M 16/167;
(Continued)

(56) References Cited

U.S. PATENT DOCUMENTS 2,199,724 A * 5/1940 Herbert ............. A61M 16/1075
128/204.17
3,434,471 A * 3/1969 Liston ................... A61M 16/00
128/203.14
(Continued)

FOREIGN PATENT DOCUMENTS

EP 0 013 170 4/1983
EP 1 338 297 8/2003
(Continued)

OTHER PUBLICATIONS

Dillow "New Plastic Conducts Heat Better Than Metals, But Only in One Direction" Popular Science, published Mar. 9, 2010.*
(Continued)

*Primary Examiner* — Stephen Hobson
(74) *Attorney, Agent, or Firm* — Knobbe, Martens, Olson & Bear, LLP

(57) ABSTRACT

In some embodiments, a humidification system includes a heater base having a heater plate, a humidification chamber, and circuit. The circuit can include various conduits, including an inspiratory conduit, expiratory conduit, Y-piece, patient conduit, and/or dry conduit. In use, the chamber contains a quantity of liquid. The heater base heats the heater plate, which in turn heats the liquid to a temperature that causes at least some of the liquid to become vapor, thereby humidifying the gases within the chamber. The gas is delivered to the patient via the inspiratory conduit. Various features can help control the system and ensure the patient receives gases having the desired conditions. These features can be used individually or in various combinations and subcombinations both in existing humidification systems and improved systems for respiratory humidification, laparoscopy, and other purposes.

27 Claims, 15 Drawing Sheets

(51) Int. Cl.
*A61M 16/10* (2006.01)
*A61M 16/00* (2006.01)

(52) U.S. Cl.
CPC ........ *A61M 16/1075* (2013.01); *A61M 16/16* (2013.01); *A61M 16/167* (2014.02); *A61M 16/168* (2014.02); *A61M 16/0833* (2014.02); *A61M 16/108* (2014.02); *A61M 16/109* (2014.02); *A61M 16/1085* (2014.02); *A61M 16/1095* (2014.02); *A61M 2016/003* (2013.01); *A61M 2016/102* (2013.01); *A61M 2205/18* (2013.01); *A61M 2205/215* (2013.01); *A61M 2205/3306* (2013.01); *A61M 2205/3331* (2013.01); *A61M 2205/3368* (2013.01); *A61M 2205/3389* (2013.01); *A61M 2205/3561* (2013.01); *A61M 2205/3569* (2013.01); *A61M 2205/3592* (2013.01); *A61M 2205/3673* (2013.01); *A61M 2205/502* (2013.01); *A61M 2205/581* (2013.01); *A61M 2205/583* (2013.01); *A61M 2205/584* (2013.01); *A61M 2205/6018* (2013.01); *A61M 2205/6054* (2013.01); *A61M 2205/75* (2013.01); *A61M 2205/82* (2013.01); *A61M 2205/8206* (2013.01); *A61M 2205/8293* (2013.01); *A61M 2209/10* (2013.01); *A61M 2230/50* (2013.01)

(58) Field of Classification Search
CPC ............ A61M 16/168; A61M 16/0875; A61M 16/16; A61M 2205/75; A61M 16/1095; A61M 2205/581; A61M 2205/3368; A61M 2205/3569; A61M 16/0833; A61M 2205/3306; A61M 2209/10; A61M 2205/8293; A61M 16/1085; A61M 2205/3592; A61M 2205/6054; A61M 16/108; A61M 2205/82; A61M 2205/18; A61M 2205/3389; A61M 2205/8206; A61M 2205/3331; A61M 2205/584; A61M 2230/50; A61M 2205/583; A61M 2016/003; A61M 2205/3673; A61M 2205/3561; A61M 2016/102; A61M 2205/215; A61M 2205/502; A61M 2205/6018
See application file for complete search history.

(56) References Cited

U.S. PATENT DOCUMENTS

| | | | |
|---|---|---|---|
| 3,434,771 A | 3/1969 | Alvarez | |
| 3,766,914 A * | 10/1973 | Jacobs | A61M 16/00 128/200.13 |
| 3,906,604 A | 9/1975 | Kakizaki et al. | |
| 3,990,441 A * | 11/1976 | Hoyt | A61M 16/1075 128/200.18 |
| 4,201,737 A * | 5/1980 | Carden | A61M 16/16 128/200.21 |
| 4,272,014 A * | 6/1981 | Halfpenny | B64D 13/00 236/44 B |
| 4,303,601 A * | 12/1981 | Grimm | A61M 16/1075 261/142 |
| 4,489,777 A | 12/1984 | Del Bagno et al. | |
| 4,597,917 A * | 7/1986 | Lunsford | A61M 16/1075 128/200.11 |
| 4,621,632 A * | 11/1986 | Bartels | A61M 16/1075 128/203.17 |
| 4,829,997 A | 5/1989 | Douwens et al. | |
| 4,861,523 A | 8/1989 | Beran | |
| 5,176,856 A * | 1/1993 | Takahashi | B01F 3/0407 219/505 |
| 5,677,982 A * | 10/1997 | Levine | F24F 1/02 392/391 |
| 5,792,041 A * | 8/1998 | Kobayashi | A61G 11/00 600/22 |
| 6,078,730 A | 6/2000 | Huddart et al. | |
| 6,158,502 A | 12/2000 | Thomas | |
| 6,260,959 B1 | 7/2001 | Takahashi | |
| 6,349,722 B1 * | 2/2002 | Gradon | A61M 16/1095 128/203.17 |
| 6,523,538 B1 | 2/2003 | Wikefeldt | |
| 7,467,786 B2 * | 12/2008 | Jae-Bong | F24F 6/02 261/81 |
| 7,722,016 B2 * | 5/2010 | Bradley | A61M 16/167 261/70 |
| 8,028,693 B2 | 10/2011 | Trevor-Wilson et al. | |
| 8,042,535 B2 | 10/2011 | Kenyon et al. | |
| 8,511,305 B2 * | 8/2013 | Liu | A61M 16/1075 128/204.17 |
| 2003/0154977 A1 * | 8/2003 | White | A61M 16/1075 128/203.26 |
| 2006/0005622 A1 * | 1/2006 | Burdi | F04D 15/0218 73/304 C |
| 2006/0055069 A1 * | 3/2006 | DiMatteo | A61M 16/16 261/142 |
| 2006/0137445 A1 * | 6/2006 | Smith | A61M 16/1075 73/204.22 |
| 2007/0079826 A1 * | 4/2007 | Kramer | A61M 16/109 128/200.14 |
| 2008/0042304 A1 * | 2/2008 | Koch | A61M 16/1075 261/141 |
| 2008/0110458 A1 * | 5/2008 | Srinivasan | A61M 11/041 128/203.26 |
| 2008/0257346 A1 * | 10/2008 | Lathrop | A61M 16/0066 128/204.17 |
| 2009/0000620 A1 * | 1/2009 | Virr | A61M 16/1075 128/203.27 |
| 2009/0025723 A1 | 1/2009 | Schobel et al. | |
| 2009/0056712 A1 * | 3/2009 | Cortez, Jr. | A61M 16/08 128/203.26 |
| 2009/0056716 A1 * | 3/2009 | Carrier | A61M 15/00 128/204.15 |
| 2009/0093753 A1 * | 4/2009 | Speasman | A61M 13/003 604/26 |
| 2009/0107980 A1 * | 4/2009 | Andel | A61M 16/1075 219/443.1 |
| 2009/0205659 A1 * | 8/2009 | Belluzzi | A61M 16/1045 128/204.17 |
| 2009/0220222 A1 * | 9/2009 | Rabin | A01M 1/2077 392/396 |
| 2009/0320840 A1 | 12/2009 | Klasek et al. | |
| 2010/0083965 A1 | 4/2010 | Virr et al. | |
| 2010/0132707 A1 * | 6/2010 | Muller | A61M 16/1075 128/204.17 |
| 2010/0307495 A1 * | 12/2010 | Kepler | A61M 16/0057 128/203.26 |
| 2011/0017212 A1 * | 1/2011 | Kenyon | A61M 16/0051 128/203.26 |
| 2011/0146679 A1 * | 6/2011 | Heesch | A61M 16/1075 128/204.17 |
| 2011/0162649 A1 * | 7/2011 | Potharaju | A61M 16/0066 128/203.26 |
| 2011/0303541 A1 | 12/2011 | Garimella et al. | |
| 2012/0248636 A1 * | 10/2012 | Fridberg | A61M 16/1075 261/128 |
| 2013/0174842 A1 * | 7/2013 | Young | A61L 9/032 128/203.14 |
| 2014/0232024 A1 * | 8/2014 | Church | A61M 16/16 261/141 |
| 2014/0299126 A1 * | 10/2014 | Buechi | A61M 16/16 128/202.22 |

(56) References Cited

U.S. PATENT DOCUMENTS

2015/0151074 A1* 6/2015 Hermez ............ A61M 16/0875
128/203.27
2016/0256657 A1  9/2016 Klasek et al.

FOREIGN PATENT DOCUMENTS

| | | |
|---|---|---|
| GB | 1 450 097 | 9/1976 |
| GB | 2 072 526 | 10/1981 |
| JP | H08-109984 | 4/1996 |
| WO | WO 1986/002566 | 5/1986 |
| WO | WO 2004/026382 | 4/2004 |
| WO | WO 2006/017161 | 2/2006 |
| WO | WO 2008/024001 | 2/2008 |
| WO | WO 2008/056993 | 5/2008 |
| WO | WO 2009/015410 | 2/2009 |
| WO | WO 2009/022004 | 2/2009 |
| WO | WO 2009/107070 | 9/2009 |
| WO | WO 2011/077250 | 6/2011 |
| WO | WO 2013/147623 | 10/2013 |

OTHER PUBLICATIONS

Jul. 15, 2013 International Search Report for PCT Application No. PCT/NZ2013/000054 Filed on Mar. 28, 2013.

* cited by examiner

HUMIDIFICATION SYSTEM

CROSS-REFERENCE TO RELATED APPLICATIONS

The present application is a National Phase Application of PCT International Application Number PCT/NZ2013/000054, filed Mar. 28, 2013, which claims priority benefit of U.S. Provisional Application Nos. 61/618,573, filed Mar. 30, 2012, and 61/785,644, filed Mar. 14, 2013, each of which is hereby incorporated by reference herein.

BACKGROUND

Field of the Invention

The present disclosure generally relates to humidification systems for providing humidified gases to patients.

Description of the Related Art

Many gas humidification systems deliver heated and humidified gases for various medical procedures, including respiratory treatment, laparoscopy, and the like. These systems can be configured to control temperature, humidity and flow rates through the use of sensors. Various components of such a system can also include features designed to help control the system and/or help provide patients with gases having desired characteristics.

SUMMARY

In some embodiments, a humidification system includes a heater base having a heater, a humidification chamber, and a circuit. The circuit can include various conduits, including an inspiratory conduit, expiratory conduit, Y-piece, patient conduit, and/or dry conduit. In use, the humidification chamber contains a quantity of liquid. The heater base energizes the heater, which in turn heats the liquid to a temperature that causes at least some of the liquid to become vapor through one or more of evaporation, vaporization and/or atomization, thereby humidifying the gases as the gases pass through the chamber over the liquid. The humidified gas can be delivered to the patient via the inspiratory conduit. In some embodiments, the humidification system includes a flow source.

In some embodiments, a humidification circuit can include conduits having heating wires or other types of heaters or heat generators. In some configurations, the humidification circuit can comprise a construction where the inspiratory conduit and the expiratory conduit are formed as a single conduit. The single conduit can be in such a way that the heating wire is not severed and runs substantially continuously along both conduits. In some configurations, the circuit comprises coaxial conduits having a breathable outer conduit. In some embodiments, a conduit includes an inner tube configured to reduce a compressible volume in the conduit. In some embodiments, a conduit can include a hot bead, a temperature sensor, and a flow sensor, and a humidity of gases flowing through the conduit can be determined based on power dissipation, temperature, and flow measurements.

In some embodiments, a humidification chamber is coupled to a pump configured to add or remove liquid to/from the chamber, thereby allowing the chamber to have a variable compressible volume. In some embodiments, a humidification chamber includes one or more floats that function to help reduce or eliminate the likelihood of the liquid level in the chamber rising too high. The float(s) can be at least partially made of an absorbent or hydrophilic material to lessen a reduction in the surface area of liquid in the chamber caused by the presence of the float(s). In some embodiments, a humidification chamber wall can be at least partially made of a hydrophobic or hydrophilic material to lessen a loss of humidity by reducing condensation build-up.

In some embodiments, various types of sensors are provided in a humidification system. For example, temperature can be sensed via suitable temperature sensors, one or more fiber-optic cables, and/or ultrasonic reflection. In some embodiments, one or more sensors can communicate with one or more processors wirelessly to help control the system.

In a further aspect the invention consists in components as herein described with reference to any one or more of the drawings.

In summary, the disclosure may be described according to the following numbered clauses:

Clause 1. A humidification apparatus comprising: a humidification chamber configured to hold a volume of liquid, the chamber comprising: a side wall; a top wall connected to the side wall; and an inlet and an outlet extending through at least one of the top wall and the side wall, a gas flow path defined within the humidification chamber between the inlet and the outlet; at least a first portion of at least one of the side wall and the top wall being configured to allow for increased heat loss from gases in the gas flow path compared to a second portion of at least one of the side wall and the top wall such that heat loss from the gases in the gas flow path can lower a temperature of the gases.

Clause 2. The humidification apparatus of Clause 1, wherein the first portion that is configured to allow for increased heat loss comprises a material having a thermal conductivity higher than the second portion of the at least one of the side wall and the top wall.

Clause 3. The humidification apparatus of Clause 1 or 2, wherein the first portion that is configured to allow for increased heat loss is positioned in a region of the at least one of the side wall and the top wall configured to be above a normal water operating level in use.

Clause 4. The humidification apparatus of any of Clauses 1-3 further comprising a humidifier comprising a heater plate, the humidifier configured to receive the humidification chamber so that a bottom surface of the chamber at least partially contacts the heater plate, the heater plate being configured to vibrate to disturb the volume of liquid within the humidification chamber to inhibit formation of a boundary layer of gases in the flow path adjacent the liquid.

Clause 5. The humidification apparatus of any of Clauses 1-4 further comprising a pump in fluid communication with the humidification chamber, the pump being configured to remove liquid from the chamber to vary a compressible volume of the humidification chamber to allow a given humidification chamber to be adapted for patients requiring respiratory therapy of different tidal volumes or frequency.

Clause 6. The humidification apparatus of any of Clauses 1-5, further comprising a conduit comprising: an outer tube and an inner tube disposed within the outer tube; wherein a gas flow path is defined either within the inner tube or between the outer tube and the inner tube, the inner tube decreasing an effective volume of the conduit to reduce compliance of the conduit.

Clause 7. The humidification apparatus of Clause 6, wherein the gas flow path is defined within the inner tube and a space between the outer tube and the inner tube is at least partially filled with a fluid to reduce compliance of the conduit.

Clause 8. The humidification apparatus of any of Clauses 1-7 further comprising an ultraviolet light source configured to expose the liquid to ultraviolet light to reduce the likelihood of contamination.

Clause 9. The humidification apparatus of Clause 8, wherein the ultraviolet light source is contained within a sleeve positioned within the humidification chamber.

Clause 10. The humidification apparatus of Clause 8, wherein the ultraviolet light source is positioned within a liquid reservoir configured to supply the liquid to the humidification chamber.

Clause 11. The humidification apparatus of any of Clauses 1-10 further comprising at least one water level sensor comprising a pattern of conductive material printed on a surface of the apparatus.

Clause 12. The humidification apparatus of any of Clauses 1-11 further comprising at least one color changing indicator coupled to or forming at least part of at least one component of the humidification apparatus, the indicator being configured to change color in response to changes in a temperature and/or humidity of gases flowing in the component.

Clause 13. The humidification apparatus of Clause 12, wherein the at least one color changing indicator is overlaid onto the component of the humidification apparatus.

Clause 14. The humidification apparatus of Clause 12, wherein the at least one color changing indicator replaces a portion of the component.

Clause 15. The humidification apparatus of any of Clauses 12-14 further comprising a camera positioned to monitor the at least one color changing indicator.

Clause 16. The humidification apparatus of Clause 15, wherein the camera is configured to monitor one or more of humidity, flow rate, temperature, pressure, and/or gas content of gases flowing in the component.

Clause 17. A humidification apparatus comprising: a humidification chamber configured to hold a volume of liquid, the chamber comprising: a side wall; a top wall connected to the side wall; a bottom surface connected to the side wall; and an inlet and an outlet formed on at least one of the top wall, the side wall and the bottom surface, a gas flow path defined between the inlet and the outlet; and the bottom surface of the humidification chamber comprising a thermally conductive pliable material.

Clause 18. The humidification apparatus of Clause 17, wherein the thermally conductive material pliable comprises aluminum foil.

Clause 19. The humidification apparatus of Clause 17 or 18 further comprising a chamber heater plate disposed within the humidification chamber.

Clause 20. The humidification apparatus of Clause 19 further comprising a humidifier comprising a heater plate, the humidifier configured to receive the humidification chamber so that the chamber heater plate is thermally connected to the heater plate of the humidifier.

Clause 21. The humidification apparatus of Clause 19 or 20, wherein the chamber heater plate comprises a heater wire configured to heat the chamber heater plate.

Clause 22. A humidification apparatus comprising: a Y-piece comprising: a first branch configured to be coupled to an inspiratory limb of a breathing circuit assembly; a second branch configured to be coupled to an expiratory limb of a breathing circuit assembly; a third branch configured to be coupled to a patient supply conduit or a patient interface; and a heating element extending along or about at least a portion of the Y-piece.

Clause 23. The humidification apparatus of Clause 22, wherein the heating element comprises one or more heater wires.

Clause 24. The humidification apparatus of Clause 22 or 23 further comprising at least one conduit configured to be coupled to the Y-piece.

Clause 25. The humidification apparatus of Clause 24, wherein the conduit comprises a cut extending axially partially through the conduit to form the inspiratory and expiratory limbs and the first and second branches of the Y-piece are configured to be coupled to ends of the inspiratory and expiratory limbs, respectively, adjacent the cut, wherein the cut is made to not sever the heating means so that the heating means runs uninterrupted along both the inspiratory and expiratory limbs.

Clause 26. The humidification apparatus of any of Clauses 22-25 further comprising at least one color changing indicator coupled to or forming part or all of the Y-piece, the indicator configured to change color in response to changes in a temperature and/or humidity of gases flowing in the component.

Clause 27. The humidification apparatus of Clause 26, wherein the at least one color changing indicator is overlaid onto the Y-piece.

Clause 28. The humidification apparatus of Clause 26, wherein the at least one color changing indicator replaces a portion of the Y-piece.

Clause 29. The humidification apparatus of any of Clauses 26-28, further comprising a camera positioned to monitor the at least one color changing indicator.

Clause 30. The humidification apparatus of Clause 29, wherein the camera is configured to monitor one or more of humidity, flow rate, temperature, pressure, and/or gas content of gases flowing in the component.

Clause 31. A method of determining a humidity of gases flowing in a humidification system, the method comprising: measuring a flow rate of the gases; measuring a temperature of the gases; measuring power dissipation using a power meter configured to measure power used by a heated thermister to maintain the thermister at a predetermined temperature; and determining the humidity of the gases using the measured flow rate, temperature, and power dissipation.

Clause 32. A humidification apparatus comprising: a chamber configured to hold a volume of liquid and comprising: an outer body defining a chamber; an inlet port defining a passage into the chamber; an outlet port defining a passage out of the chamber; a gas flow path defined between the inlet port and the outlet port; a flow rate sensor positioned at the inlet port; at least one thermistor probe positioned at the inlet port; and at least one thermistor probe positioned at the outlet port; and a humidifier configured to receive the chamber, the humidifier comprising a processor configured to receive temperature, flow rate, and heat dissipation data from the flow rate sensor and thermistor probes and use the data to determine humidity gained by gases traveling in the flow path between the inlet port and the outlet port.

Clause 33. A breathing circuit assembly comprising one or more conduits having means for measuring a temperature of gases flowing within the conduits and/or an ambient temperature surrounding the conduits at a plurality of positions in the circuit assembly.

Clause 34. The breathing circuit assembly of Clause 33, wherein the means for measuring temperature comprises one or more printed temperature sensors comprising a pattern of conductive material printed on an inner or outer surface of one or more of the conduits.

Clause 35. The breathing circuit assembly of Clause 33 or 34, wherein the means for measuring temperature comprises one or more fiber optic cables extending longitudinally along an outside of one or more conduits and/or within one or more conduits.

Clause 36. The breathing circuit assembly of any of Clauses 33-35, wherein the means for measuring temperature comprises: an acoustic wave producer; a wave receiver spaced from the acoustic wave producer; and a plate positioned between the acoustic wave producer and the wave receiver, one ore more characteristics of the plate configured to change in response to changes in temperature.

Clause 37. A humidification apparatus comprising: the breathing circuit assembly of any of Clauses 33-36; a humidifier comprising a processor; and a wireless communication means configured to allow for communication and transfer of data and/or instructions between the means for measuring temperature and the processor.

Clause 38. The humidification apparatus of Clause 37, wherein the means for measuring temperature comprises power generation means.

Clause 39. The humidification apparatus of Clause 38, wherein the power generation means comprises a thermal energy gathering means configured to generate power from thermal energy in gases flowing within the breathing circuit assembly.

Clause 40. The humidification apparatus of Clause 38 or 39, wherein the power generation means comprises a pressure energy gathering means configured to generate power from vibrations within the breathing circuit assembly.

Clause 41. The humidification apparatus of any of Clauses 38-40, wherein the power generation means comprises a radiation energy gathering means.

Clause 42. A humidification apparatus comprising: a humidification chamber configured to hold a volume of liquid; a humidifier comprising a processor and a heater plate, the humidifier configured to receive the chamber so that a bottom surface of the chamber contacts the heater plate; and a temperature sensor configured to be positioned on a patient's skin in use to measure the patient's skin temperature and connected to the processor via a wired or wireless connection; wherein the processor is configured to receive data from the temperature sensor.

Clause 43. The humidification apparatus of Clause 42, wherein the processor is configured to adjust one or more operating parameters of the humidification apparatus based on the data.

Clause 44. The humidification apparatus of Clause 43, wherein the one or more operating parameters comprise a temperature of the heater plate and/or the volume of liquid in the chamber.

Clause 45. The humidification apparatus of Clause 42, wherein the humidifier further comprises a display and the processor is configured to display the patient's skin temperature on the display.

Clause 46. A humidification chamber comprising: an outer body defining a chamber; one or more ejectors disposed within the chamber and configured to eject a controlled quantity of liquid into the chamber; and heating means configured to heat the liquid ejected from the one or more ejectors to a temperature sufficient to cause the liquid to evaporate.

Clause 47. The humidification chamber of Clause 46, wherein the heating means comprises a heater plate disposed within the chamber and the ejectors eject the liquid onto the heater plate.

Clause 48. The humidification chamber of Clause 46, wherein the heating means comprises one or more heaters positioned at or proximate a nozzle of each of the one or more ejectors.

Clause 49. A humidification system comprising: a humidifier comprising a processor, a first memory storing a control program or algorithm, and a first data transfer connection; and a second memory and a second data transfer connection coupled to a component of the humidification system, the second memory storing data configured to update or replace at least a portion of the control program or algorithm stored in the first memory; wherein in use the second data transfer connection is operatively connected to the first data transfer connection to form an operative connection between the second memory and the processor and/or the first memory.

Clause 50. The humidification system of Clause 49, wherein the second memory and second data transfer connection are coupled to a humidification chamber configured to be received by the humidifier.

Clause 51. The humidification system of Clause 49, wherein the second memory and second data transfer connection are coupled to a conduit of a breathing circuit assembly.

Clause 52. The humidification system of Clause 51, further comprising a humidification chamber comprising a third data transfer connection, wherein in use, the second data transfer connection of the breathing circuit assembly is operatively coupled to the third data transfer connection of the humidification chamber, which is operatively coupled to the first data transfer connection of the humidifier.

Clause 53. The humidification system of any of Clauses 49-52, wherein one of the first and second data transfer connections is an RFID tag, and the other of the first and second data transfer connections is an RFID interrogator to allow the first and second data connections to be operatively coupled without physical contact.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description which is given by way of example only.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application and/or statements of invention, individually or collectively, and any or all combinations of any two or more said parts, elements features or statements of invention, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

These and other features, aspects and advantages of the present disclosure will be described with reference to the following drawings, which are illustrative but should not be limiting of the present disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Various features as described herein can help control the system and increase the likelihood of the patient receiving gases having desired conditions. The features described herein can be used individually or in various combinations and subcombinations in existing humidification systems and/or in improved systems for respiratory humidification, laparoscopy, and other purposes.

Overview of Humidification Systems

Figure 1:
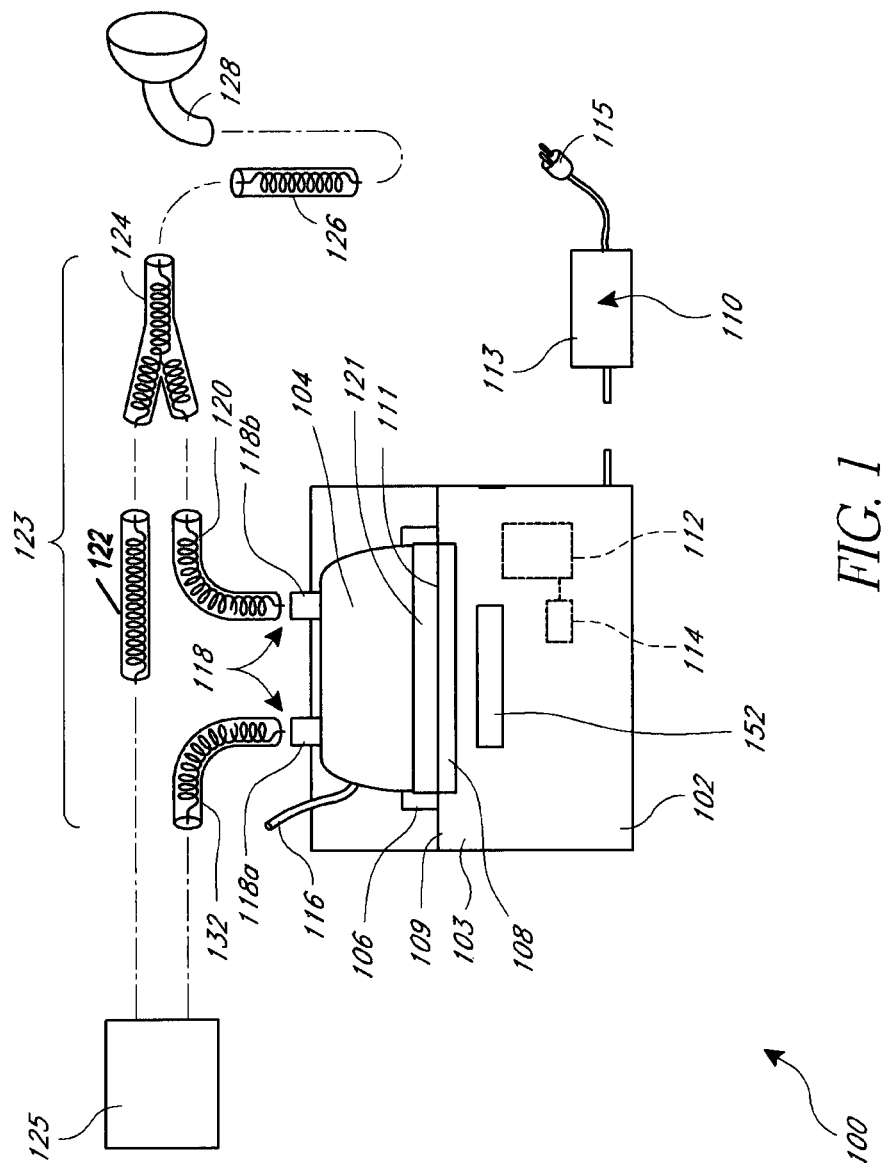
FIG. 1 illustrates various embodiments of humidification systems.

With reference to FIG. 1, an example embodiment of a humidification system 100 is illustrated therein. The humidification system 100 can have any suitable configuration. By way of some examples, in some applications, the humidification system 100 can be used with breathing treatments, positive pressure apparatus, noninvasive ventilation, and surgical procedures, including but not limited to laparoscopy. Desirably, the humidification system 100 can be adapted to supply humidity or water vapor to a supply of gases. In some configurations, the humidification system 100 can comprise a passover humidifier, a blow-by humidifier, a bubble through humidifier (e.g., Wolfe bottle, AquinOx), a diffuser-based humidifier, a nebulizer or the like. In some configurations, the humidification system 100 can be heated or unheated, depending upon the implementation desired. In some configurations, a flow source can be integrated with the humidification system 100.

Humidifier

Figure 2:
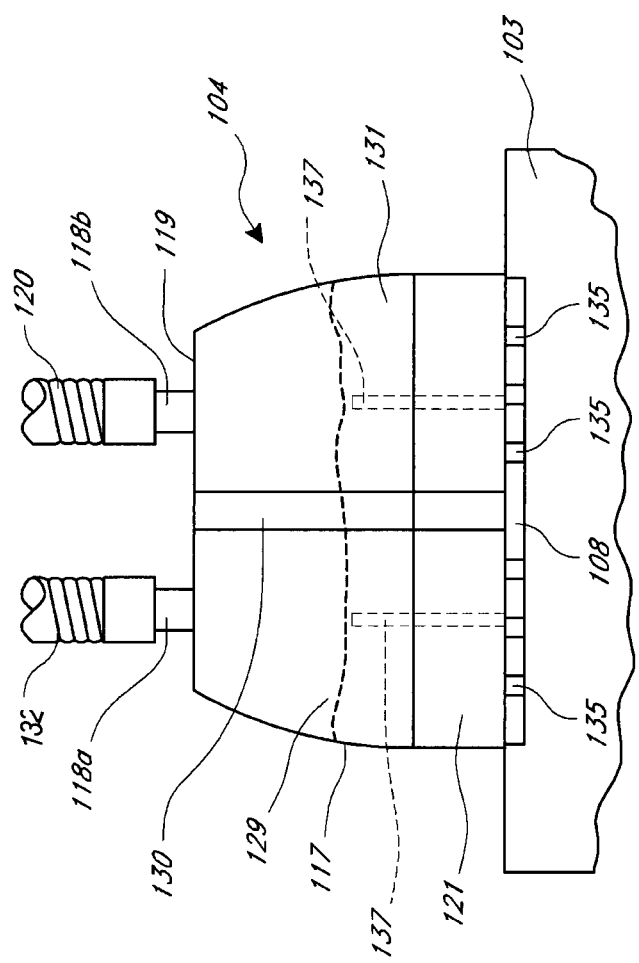
FIG. 2 partially illustrates an embodiment of a humidification system.

With reference to FIG. 1, the illustrated humidification system comprises a heated passover humidifier. The humidifier can be configured as set forth in U.S. Provisional Patent Application No. 61/611,331, filed on Mar. 15, 2012, which is hereby incorporated by reference in its entirety. The illustrated humidification system comprises a humidifier 102. The humidifier 102 receives a humidification chamber 104, as also shown in FIG. 2. In some configurations, the humidifier 102 comprises a housing 103 that receives the humidification chamber 104. The housing 103 can extend upward beyond the humidification chamber 104 in some configurations. In some configurations, the housing 103 can extend over top of at least a portion of the humidification chamber 104. In some configurations, the housing 103 can overlie the entire humidification chamber 104. In some configurations, the housing 103 completely or substantially completely enshrouds the humidification chamber 104.

With reference again to Figure, 1, the humidifier 102 comprises a heater plate 108. The heater plate 108 can have any suitable configuration. The heater plate 108 preferably is positioned along a generally horizontal upper surface 109. In some configurations, the heater plate 108 is generally flush with, slightly recessed below or positioned slightly above the surface 109. In some configurations, a securing collar 106 extends at least partially around the heater plate 108. The securing collar 106 can be used to secure the humidification chamber 104 in position on the heater plate 108.

In some configurations, the heater plate 108 comprises an upper surface 111 that is accessible. In other words, the heater plate 108 preferably is exposed such that the upper surface 111 of the heater plate 108 is not concealed by the upper surface 109 of the housing 103. In some arrangements, at least the upper surface 111 of the heater plate 108 can be covered by a protective covering. In some arrangements, additional heating components can extend upward such that the additional heating components can provide additional heat transfer to the humidification chamber. In some configurations, one or more such additional heating components can generally encircle at least a vertically extending portion of the chamber 104 in a sleeve-like manner.

The heater plate 108 can comprise any suitable heating element. The heating element can be energized or powered by the humidifier 102, for example but without limitation. When the heating element of the heater plate 108 is energized or powered, the heater plate 108 can increase in temperature, for example, to a predetermined or settable temperature. The temperature can be settable or adjustable but preferably is sufficiently high to allow heat transfer from the heater plate 108 to the humidification chamber 104 to heat the liquid therein sufficiently to humidify a flow of gases passing through the humidification chamber 104.

In use, when the gases flow over the liquid, a boundary layer of heated gases can form within the humidifier chamber 104. A bounding surface can be considered to be the water surface and generally refers to the thermal and velocity profiles of the gases flowing over the water surface. The region of unchanged temperature profile can be called the thermally developed region while the region of flow over which the thermal boundary develops can be called the thermally developing region. The heat transfer coefficient is greatest in the developing region of the thermal boundary region. This is believed to be because the fluid particles in contact with the bounding surface (e.g., the water) come to a stop and generally assume the surface temperature of the water in the fully developed region. As such, the temperature profile generally becomes uniform.

Accordingly, in the humidifier of FIG. 2, the boundary layer can form on top of or adjacent the liquid surface within the humidification chamber 104 as gas particles near the liquid surface flow over the surface more slowly due to drag and those in contact with the liquid surface come to a stop. This can result in a lower liquid surface temperature due to heat loss to the boundary layer. The rate of evaporation is therefore lowered. Such a boundary layer can inhibit the production of vapor during heating of the liquid, which is of particular concern when high gas flow rates are desired. In some embodiments, to help reduce the likelihood of such a boundary layer, the heater plate 108 and/or at least part of the chamber 104 can vibrate. The vibration disturbs the liquid within the chamber 104 and inhibits the formation of a boundary layer. The movement of the liquid helps dissipate the boundary layer, thereby helping to reduce heat loss and maintain the temperature of the liquid, thereby increasing the production of humidified gases through evaporation. In some embodiments, the heater base 102 can include a motor with an off-center weight and/or a suitably configured piezoelectric element to cause the water within the chamber 104 to vibrate.

With reference again to FIG. 1, the humidification system 100 can further include a power source 110. In use, the power source 110 supplies power to the humidifier 102, which in turn energizes the heater plate 108, causing the heater plate 108 to heat to a desired temperature. In some configurations, the power source 110 can be integrated into the housing 103. In some configurations, the power source 110 can be coupled to the housing 103. Preferably, however, the power source 110 is external to the housing 103 and is electrically connected to the humidifier 102. A separate power source 110 advantageously allows for the humidifier 102 to have a lower weight, reduces heat produced within the humidifier 102, and provides for ease of servicing.

The power source 110 provides power to the humidifier 102. The power from the power source 110 can be provided from the humidifier to other components, if desired. In some embodiments, the power source 110 can be used to directly power multiple separate devices. The power source 110 can comprise a transformer 113 and a mains connection 115, for example but without limitation. The power source 110 can be a switch mode power supply. The power source 110 can connect to the humidifier 102 via a conventional two-pin or three-pin electrical connector. The power source 110 can be connected to mains power. Alternatively or additionally, the power source 110 may have a power storage device (such as one or more batteries), a power generator (such as one or more solar cells) and/or a surge protector or the like.

The humidifier 102 can include one or more processors 112 and one or more associated memories 114, which can help control heating of the heater plate 108 among other things.

Humidification Chamber

The humidification chamber 104 can be configured to contain a volume of liquid, for example, water. The example humidification chamber illustrated in FIG. 2 comprises at least one side wall 117 and at least one top wall 119.

At least a portion 130 of at least one of the side wall 117 and top wall 119 of the chamber 104 can comprise a transparent material, for example, glass, polycarbonate or the like, to allow a user to easily view and assess the quantity of liquid in the chamber 104. In some configurations, a non-transparent or non-translucent material may be used to form part 131 of the chamber 104. In such configurations, preferably the transparent part 130 can define a window or other structure to provide an indication of liquid level.

In some configurations, at least a portion 129 of at least one of the side wall 117 and the top wall 119 can be formed of a material having a thermal conductivity higher than that of the rest of the chamber, and/or preferably higher than that of polycarbonate. Preferably, the portion 129 is formed in a region that generally will be higher than a normal water operating level. In other words, in some configurations, at least a portion of the region above the normal water level will have an increased thermal conductivity relative to the region that will normally be in contact with water. In such applications, increased heat loss can occur through the portion 129 of at least one of the side wall 117 and the top wall 119. The heat loss enables the gases to be cooled before entering the inspiratory conduit 120. This in turn enables the operating temperature of the water in the chamber 104 to be higher than otherwise possible, thereby enhancing vaporization of the water and humidification of the gases passing through the chamber 104 while the gas delivered to the patient can be maintained at a suitable temperature.

The chamber 104 can include an opening or port for the connection of a liquid conduit 116 to the chamber 104. Alternatively, as shown in FIG. 1, the liquid conduit 116 can be integrally formed with or permanently coupled to the chamber 104. In use, the liquid conduit 116 conveys a liquid, for example, water, from a liquid source to the chamber 104. The chamber 104 and/or liquid conduit 116 can include any suitable structure to restrict or limit the flow and/or quantity of liquid in the chamber 104 and/or liquid conduit 116.

In some configurations, the liquid source can be a water bag and the water bag can be connected to the chamber 104 with the conduit 116, for example. In some configurations, the liquid source can be integrated into the humidifier 102. In some configurations, the liquid source may include tap or mains water. In such an embodiment, a water filter may be included between the liquid source and the chamber 104 to reduce the likelihood of minerals, contaminants or the like being introduced into the chamber 104 and potentially damaging or impeding the performance of components of the system 100.

In configurations in which the liquid source is integrated into the humidifier 102 or the liquid conduit 116 passes through the housing 103 of the humidifier 102, the liquid can be exposed to ultraviolet light to reduce the likelihood of contamination by bacteria and/or fungi, for example but without limitation. In some configurations, the ultraviolet light can comprise, for example, a UV-B or UV-C light source, which can be a low or medium pressure mercury vapor lamp, excimer lamps, flashlamps with xenon and other fill mixtures, a gas discharge lamp, an LED (e.g., AlGaN-based DUV LEDs grown over sapphire substrates with peak emission wavelengths in the range of 260 nm to 340 nm), a laser, microwave driven lamps or any other suitable configuration. In some configurations, a diffuse or specular reflector can be used to amplify the effects of the ultraviolet light source while reducing the impact of the ultraviolet light source on the materials used to manufacture the humidifier 102 or its components. In some arrangements, the liquid containing member can be coated with a reflective material, such as but not limited to, any type of polytetrafluoroethylene (PTFE), expanded polytetrafluoroethylene (ePTFE), or other similar plastics or a coated, anodized or polished aluminum or other highly reflective material, including stainless steel, such as 316L stainless steel or the like.

The humidification chamber 104 itself can be exposed to ultraviolet light. In some configurations, the source for the ultraviolet light can be within the chamber 104 itself or can be within a portion of the humidifier that is exposed to the chamber 104. In configurations where the ultraviolet light source will be exposed to the liquid, the ultraviolet light source preferably is contained within a sleeve, such as a quartz sleeve for example but without limitation. The sleeve can maintain a maximum operating temperature and can reduce the likelihood of contact with the liquid. The sleeve can be positioned within the chamber or a reservoir of liquid. Where the ultraviolet light source produces UV-C radiation, the ultraviolet light source preferably is exposed to a very small region (e.g., about 200-280 nanometers) to best exploit the wavelength. In such applications, the ultraviolet light source preferably is directed to a sleeve through which the liquid passes, whether the sleeve interrupts, adjoins or envelops the conduit 116. In some configurations, the conduit 116 can be used to direct the liquid through multiple passes through ultraviolet region. In some embodiments, a shield may be provided to block at least part of the ultraviolet light from escaping the system 100 thereby reducing the risk of UV exposure to the patient and/or the operator.

A surface 121 of the humidification chamber 104 can comprise at least a portion that is formed of a thermally conductive material. In some configurations, the surface 121 can be a wall surface. In some configurations, the surface 121 can be a non-bottom surface. In some configurations, the surface 121 can be a bottom surface. In some configurations, the surface 121 can span at least a portion of the bottom surface and a side surface, for example but without limitation. Because the humidification chamber 104 is removably attachable to the humidifier 102, when the humidification chamber 104 is installed on the humidifier 102, the thermally conductive surface (e.g., the bottom surface 121) of the chamber 104 contacts the upper surface of the heater plate 108. In use, the thermally conductive material of the surface 121 transfers heat from the heater plate 108 to the contents of the chamber 104.

In some applications, the surface 121 can be formed of a thermally conductive metal, such as aluminum. Preferably, the material is sufficiently strong and easily workable, allowing for a simplified manufacturing processes. In some applications, at least a portion of the bottom surface 121 can be formed of a pliable metal foil, such as aluminum foil. In some embodiments, the heater plate 108 can include one or more holes 135 adapted to reduce the risk of air bubbles forming between the heater plate 108 and the bottom surface 121. In some applications, at least a portion of the bottom 121 of the chamber 104 can be formed of a plastic material. In some configurations, thermally conductive inserts (preferably metal) 137 can extend through the surface 121 into the humidification chamber 104. The liquid in the humidification chamber 104 can surround the inserts 137 and the inserts 137 can conduct heat from the heater plate 108 to the liquid.

In some embodiments, at least a portion of the surface 121 of the chamber 104 can be formed from a thermally conductive plastic material. For example but without limitation, the surface 121 can comprise at least a portion that is formed from a material comprising a thermally conductive filler. For example, such materials can comprise reinforcing filler(s) selected from the following list: copper, milled glass fiber, silicon carbide particles, continuous carbon fibers, discontinuous carbon fibers and a matrix selected from the following list: copper, tungsten, polymer, Al/SiC, aluminum and carbon. In some applications, the material used has a through-thickness thermal conductivity of between about 40 W/m·K and about 400 W/m·K. In some applications, the material used has a through-thickness thermal conductivity of between about 120 W/m·K and about 290 W/m·K. The use of an appropriate plastic material can advantageously reduce manufacturing costs, improve manufacturability because of the ability to mold the bottom and reduce the weight of the chamber 104.

The chamber 104 can include one or more ports 118 (118a, 118b) that allow for flow of gases into and/or out of the chamber 104. The ports 118 can protrude outwardly from the upper wall 119. In some configurations, the ports 118 can protrude outwardly from one or both of the side wall 117 and the upper wall 119. In some configurations, one or more of the ports 118 can be defined by an opening into chamber 104 without necessarily protruding upward. The embodiment illustrated in FIG. 1 includes an upwardly extending outlet port 118b and an upwardly extending inlet port 118a, both located on the top wall 119 of the chamber 104.

Circuit Assembly

A circuit assembly 123 can be connected to the ports 118. Any suitable circuit assembly 123 can be used. In some embodiments, the circuit assembly 123 can comprise an inspiratory conduit 120 coupled to and in fluid communication with the outlet port 118b of the chamber 104. In some embodiments, such as those used with a pressurized gas source 125, such as a ventilator or the like, an expiratory conduit 122 can be coupled to and in fluid communication with the gases source 125. Ends of the inspiratory conduit 120 and the expiratory conduit 122 opposite the outlet port 118b of the chamber 104 and opposite the gases source 125 can be connected to one another via a Y-piece 124, which can be coupled to a patient supply conduit 126, such as a catheter mount. The end of the patient supply conduit 126 opposite the Y-piece 124 can be coupled to an interface 128 that allows a patient to inhale gas from the humidification chamber 104 via the inspiratory conduit 120 and the patient supply conduit 126 and exhale gas via the patient supply conduit 126 and the expiratory conduit 122. Any suitable interface can be used. For example but without limitation, the interface 128 can be a nasal cannula, mask, endotracheal tube, tracheal tube, or any other suitable interface. In some embodiments, the expiratory conduit 122 and the Y-piece 124 are omitted, and the inspiratory conduit 120 can connect to the interface 128.

In some embodiments, for example as shown in FIG. 1, the circuit assembly 123 can include a supply conduit 132 coupled to the gases source 125 (e.g., a ventilator, blower, etc.) and the inlet port 118a of the chamber 104. In some configurations, the circuit assembly can include the inspiratory conduit 120 coupled to the outlet port 118b of the chamber 104 and the interface 128. In some embodiments, the circuit assembly 123 can further include the expiratory conduit 122 coupled to the interface 128 and the gases supply 125, for example as shown in FIG. 1. The inspiratory conduit 120 and the expiratory conduit 122 can be coupled to the interface 128 via the Y-piece 124 and, in some configurations, the patient conduit 126.

Preferably, one or more of the inspiratory conduit 120, the expiratory conduit 122, the Y-piece 124, the patient supply conduit 126 and the supply conduit 132 can be heated in any suitable manner. In some instances, one or more of these components can be provided with heater wires that extend along some portion of the length of the component. For example, the heater wire or heater wires can extend longitudinally within, or outside of, a lumen defined by the conduit or the heater wire or heater wires can extend helically within, or outside of, the lumen. At least one end of the heater wire or heater wires can be connected to the humidifier 102 such that the humidifier 102 can supply the power to the heater wire or heater wires. In some arrangements, the power supplied to the heater wire or heater wires can be handled by the processor 112 of the humidifier. Preferably, the heater wire is connected to the humidifier when the related conduit or other component is connected to the humidifier. For example, an electrical connection can be established when the pneumatic connection is established. More preferably, the electrical connection must be established before the pneumatic connection can be established. In some embodiments, the pneumatic connection must be established before the electrical connection can be established. In both cases, there may be a reduced risk of a spark in the gases flow.

Conduit Features

Single Tube Conduits

Figure 3A:
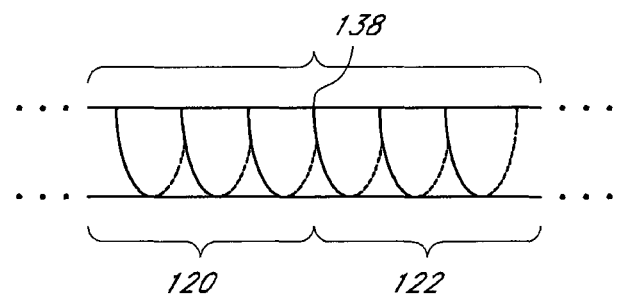
FIGS. 3A-3C illustrate limbs of a circuit formed from a single conduit.
Figure 3B:
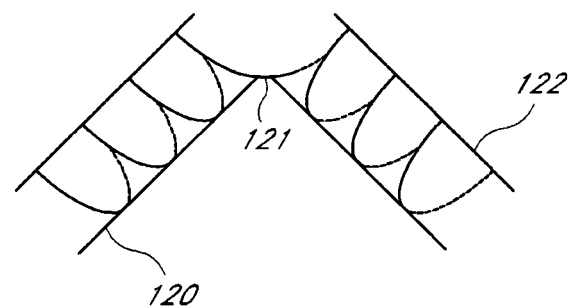
Figure 3C:
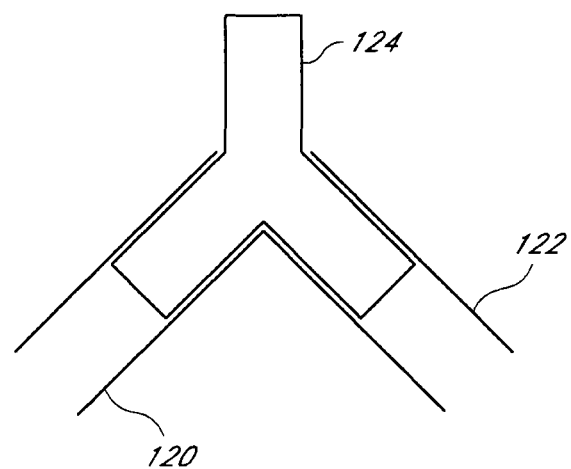

In some embodiments, one or more of the circuit assembly 123 components can be heated, for example, by heater wires 138 provided longitudinally or helically along their length. The heater wires 138 can help maintain the gases passing through the circuit assembly 123 at a desired temperature and/or humidity and help reduce or eliminate the likelihood of rain out. The heater wires 138 can be powered by the humidifier 102. In such an embodiment, the inspiratory 120 and expiratory 122 conduits may each require an electrical connection at the Y-piece 124 end of the conduits, which can increase the manufacturing cost and introduce additional failure points into the system 100. Alternatively, in some embodiments, the inspiratory 120 and expiratory 122 conduits are initially formed in one piece as shown in FIGS. 3A-3C. The combined conduit can then be cut into the constituent portions (i.e., the inspiratory conduit 120 and expiratory conduit 122) in such a way that the heater wire 138 is not severed. A single heater wire 138 therefore runs uninterrupted along the entire length of both the inspiratory 120 and expiratory 122 conduits. The arms of the Y-piece 124 can then be inserted into the cut ends of the inspiratory 120 and expiratory 122 conduits and held in place with an adhesive, an interference fit, or any other appropriate component or assembly. In some embodiments, a pivot point 121 connecting the inspiratory 120 and expiratory 122 conduits can be reinforced, either temporarily during the manufacturing process or permanently, to reduce the risk of the combined conduit being severed.

Coaxial Conduits

Figure 4A:
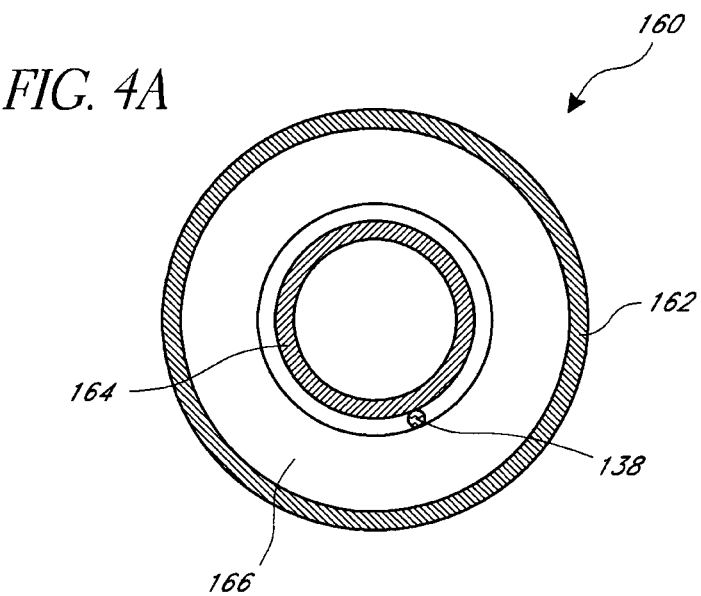
FIGS. 4A-4B illustrate example embodiments of coaxial conduits.
Figure 4B:
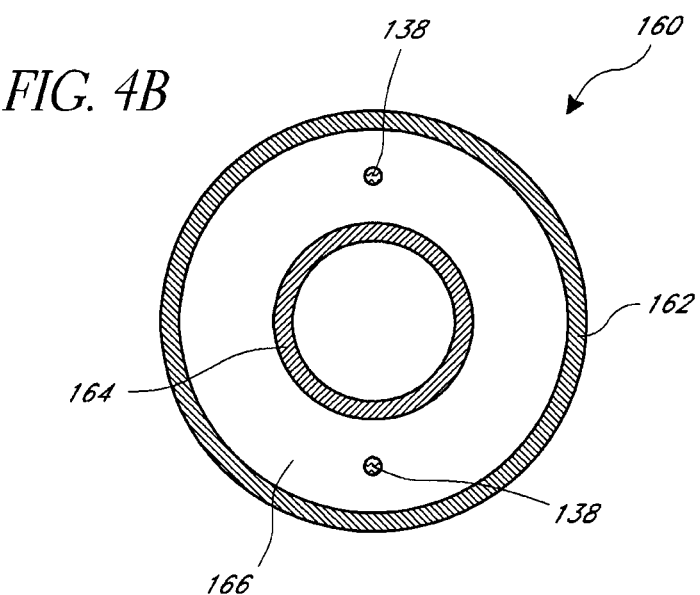

In some embodiments, one or more of the inspiratory 120, expiratory 122, patient 126, and/or dry 132 conduits can be a coaxial conduit 160, for example as shown in FIGS. 4A and 4B. A coaxial conduit 160 can include an outer conduit 162 and an inner conduit 164 with an intermediate space 166 therebetween. A fluid, for example an insulation fluid, can be circulated in the intermediate space 166. In use, gases inhaled and/or exhaled by the patient can travel within the inner conduit 164 and/or in the intermediate space 166.

The intermediate space 166 can also include one or more heater wires 138. The heater wire(s) 138 can be helically wound (as shown in FIG. 4A) or can run longitudinally along the length of the conduit (as shown in FIG. 4B). The heater wires 138 can maintain the fluid in the intermediate space 166 at a predetermined temperature or within a predetermined range of temperatures. The heater wires 138 can also or alternatively be configured to maintain the inner conduit 164 and/or outer conduit 162 at a predetermined temperature or within a predetermined range of temperatures without a fluid circulating in the intermediate space 166. In such configurations, the heater wires 138 can abut the inner conduit 164 or the outer conduit 162 as appropriate to achieve the desired temperature control.

To help reduce formation of condensate in the intermediate space 166 and/or inner conduit 164, one or both of the inner 164 and outer 162 conduits can be made at least partially of a substantially breathable material, for example, a breathable polymer. The breathable material can help equalize the humidity of the inner conduit 164, intermediate space 166, and/or the external environment. This can help the heater wires 138 operate more effectively, as there is a reduced need for the heater wires 138 to manage humidity.

Reducing Compliance of Conduit

In traditional humidification systems, the various conduits of the circuit assembly 123 have a flexible construction, which enables the conduits to be freely positioned and bent as necessary. However, this flexible construction can result in a greater compliance in the circuit assembly 123 when pressurized. In the context of breathing circuit design (e.g. conduit design), "compliance" is defined as the ratio of the volume change to the pressure change and is analogous to "stiffness" or "rigidity."

In some configurations, including in the configuration of FIG. 1, the breathing circuits are used in combination with a ventilator. In ventilation therapy, a key concern to be addressed remains minimizing "losses" in the delivered tidal volume while maintaining the desired airway pressure during inspiration. In this context, "tidal volume" is the volume of air displaced between inspiration flow and expiration flow.

Given a sufficiently high pressure gas flow, the conduits can swell, reducing the gas pressure actually delivered to the patient. This is of particular concern when using high-frequency ventilation, which requires a sufficiently high pressure in the conduits to maintain adequate gas flow. For example, for some neonatal indications, the system 100 may operate with an inhalation-exhalation cycle of about 5 Hz. Under high pressure, the conduit volume can increase to about 120% of the conduit volume at rest. Furthermore, high-frequency ventilation is typically used to deliver relatively low tidal volumes, so even small compressible volumes losses can result in a relatively large percentage reduction in delivered tidal volume.

During high-frequency ventilation, resonance of the circuit can occur, meaning an increased proportion of the energy is stored and/or absorbed by the tube, rather than reaching the patient, which can cause losses in the delivered volume or can cause an undesired variation in the actual airway pressure. The design parameters involved in minimizing or reducing "losses" in the delivered tidal volume while maintaining a desired airway pressure are compliance, compressible volume and resistance to flow, which are all interrelated.

The resistance to flow within any given conduit may be influenced by a profile of the conduit wall as well as a surface roughness combined with a diameter and a length of the conduit. These parameters influence the compressible volume of the conduit. The material properties and the profile chosen for the conduit wall and the corresponding wall thickness may influence conduit compliance. In other words, for a given compressible volume, the compliance can be higher or lower by modifying the conduit wall properties without altering the compressible volume. Similarly, a conduit with a large compressible volume will also have a higher compliance than a similar conduit that has a smaller compressible volume.

The compressible volume can be reduced by simply shortening the conduit while maintaining the same conduit construction and diameter. In many ventilator applications, however, length is an important consideration and, therefore, simply shortening the length is not often a viable option.

Figure 5A:
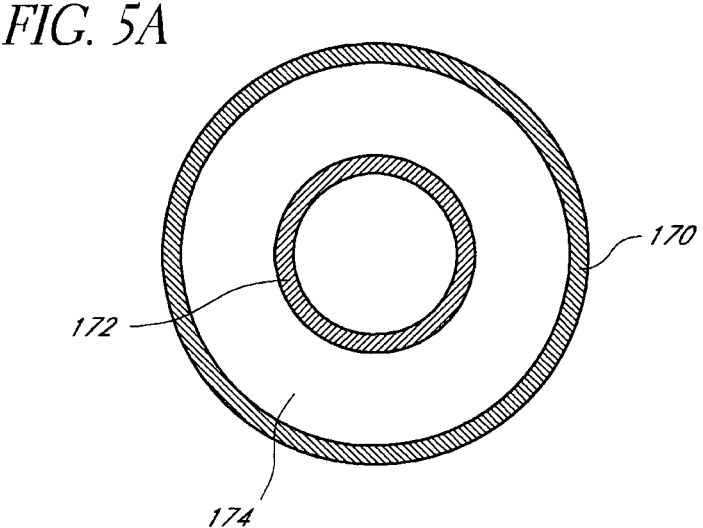
FIGS. 5A-5C illustrate examples of conduits designed to reduce compliance.

As an alternative to simply shortening the conduit length, a conduit 170 having an inner tube 172 coaxially disposed within the conduit 170, as shown in FIG. 5A, can be used for any or all of the circuit assembly 123 conduits. The inner tube 172 can be blind and can be sufficiently flexible so as to not significantly inhibit the bending of the conduit 170. In some embodiments, the inner tube 172 can be of substantially the same construction as the conduit 170 with a smaller diameter.

Figure 5B:
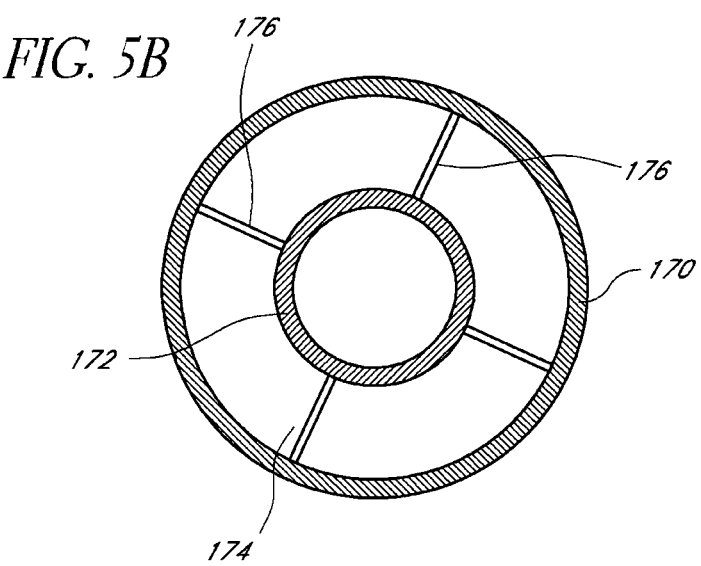
Figure 5C:
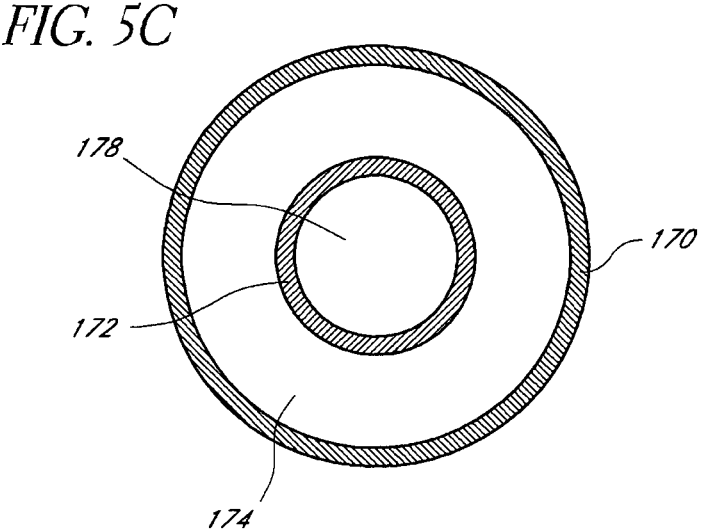

In use, gases traveling through the circuit assembly 123 pass in an intermediate space 174 between the conduit 170 and inner tube 172. Because a portion of the conduit 170 volume is taken up by the inner tube 172, the volume of the conduit 170 even during high-frequency flow can be about 100% of the volume of the conduit 170 alone at rest. In other words, the reduction in volume created by inclusion of the non-transporting inner tube effectively reduces the compliance within the conduit. In some embodiments, including the inner tube 172 within the conduit 170 enables the conduit 170 volume to be further reduced to about 60% of the volume of the conduit 170 alone. The volume varies with, and can therefore be selected by varying, the size of the inner tube 172. In some applications, the inner tube 172 can be used to reduce the proportion of the energy stored and/or absorbed by the conduit 170. With reference to FIG. 5B, the inner tube 172 can be coupled to the outer conduit 170 by multiple radial supporting structures 176. In the illustrated configuration, flow is transported through the inner tube 172 while the outer conduit 170 can be filled with stagnant air or the like. The structures 176 that extend between the inner tube 172 and the outer conduit 170 can be spring-like in characteristics or structure. The supporting structures 176 can be distributed along a central axis of the coaxial tube 172 and conduit 170. The effective spring constants of the support structures 176 can be tuned to damp oscillations of the inner tube 172 within the conduit 170, for example, due to changes in pressure within the inner tube 172. The density along the length of the tube can be determined according to the desired damping. In some configurations, rather than using radially extending spring-like structures 176, tubes or the like can be positioned radially on an outer surface of the inner tube 172. In some configurations, either as an alternative to the spring-like structures, the tubes or the like or in addition to those structures, the ends of the inner tube 172 can be anchored at both ends with spine-like structures. Such a configuration will enable the inner tube 172 to be pretensioned to a desired level, which can allow adaptation of the compliance of the conduit to suit any particular ventilator parameters.

In some configurations, where the inner tube 172 carries the flow, the space 174 between the inner tube 172 and the outer conduit 170 can be sealed at one end and pressurizable at the other end, for example but without limitation. In other words, the space 174 can be sealed and pressurized. In some configurations, the pressure can be adjusted to suit a desired performance characteristic. The pressurized gas within the space 174 can reduce the compliance of the inner tube 172 by restricting dimensional changes of the inner tube 172 that could otherwise result when the pressure in the inner tube 172 increases during ventilation, for example.

In some embodiments, rather than filling the space 174 with pressurized air or gases, the intermediate space 174 can be filled or partially filled with a non-Newtonian fluid. A Newtonian fluid is one where the stress versus strain curve is generally linear and passes through the origin when graphically represented. The slope therefore a constant, which can be defined as the fluid viscosity of the Newtonian fluid. A non-Newtonian fluid one where the relationship between shear stress and shear rate is non-linear and possibly even time-dependent. Thus, a non-Newtonian fluid can be defined as a fluid in which a constant coefficient of viscosity cannot be defined. The effects of such a fluid being placed within the space 174 would be non-linear. Including a non-Newtonian fluid in the intermediate space 174 can help reduce compliance of the conduit 170 due to the apparent increase in rigidity of the inner tube 172 in the presence of varying gas pressure within the inner tube 172. The non-Newtonian fluid could therefore damp physical oscillations of the inner tube 172 in response to pressure changes within the inner tube 172.

In some embodiments, the conduit 170 can be made of or include a fibrous material and the intermediate space 174 can be filled or partially filled with a pressurized fluid, for example, the gases being delivered, to form a structure similar to a hydrostatic skeleton. In some embodiments, the conduit 170 can be made of or include a fibrous material. The fibers of the fibrous material can be arranged as interwoven crossed helices formed around the longitudinal axis of the conduit 170 or tube 172. This arrangement can allow for bending or contraction of the conduit 170 or tube 172. Alternatively, the fibrous material can include two layers of fibers oriented perpendicularly to each other with an outer layer aligned with the longitudinal axis of the conduit 170 or tube 172. Such a configuration can be used in conjunction with a pressurized non-Newtonian fluid. This arrangement can resist extension and contraction of the conduit 170 or tube 172, thereby reducing the compliance, and, in combination with the pressurized fluid, can dampen physical disturbances of the conduit 170 or tube 172 due to pressure oscillations in the gas pathway.

Alternative Humidity Measurement

As discussed herein, it is often beneficial to measure the humidity of gases within a particular component of the system 100, for example, the circuit assembly 123, to ensure the humidity is within an expected or target range for optimal patient therapy. Based on the measured humidity level and analysis thereof, the processor 112 can adjust parameters of the system 100 to obtain a target delivery humidity, for example, 100% relative humidity at a temperature of 37° C. For example, the processor 112 may adjust a temperature of the heater plate 108 and/or heater wire(s) 138.

Some prior art humidification systems include a conventional stand-alone humidity sensor to measure humidity. However, conventional stand-alone humidity sensors can be bulky, fragile, and/or expensive. Additionally, if condensation is present on the sensor, which may occur in a high-humidity environment such as a conduit leading from a humidification chamber, or the relative humidity is near 0% or 100%, the humidity sensor may provide inaccurate measurements or fail to function entirely.

Figure 6:
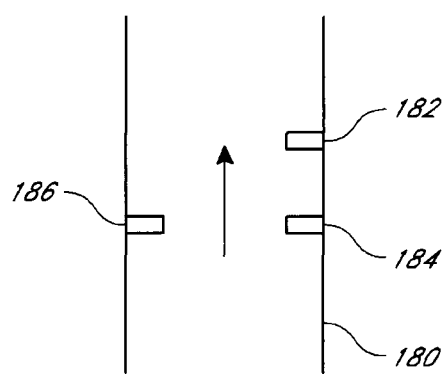
FIG. 6 illustrates a sensor system for measuring humidity.

As an alternative to a conventional humidity sensor, the humidity can be determined based on other measurements. In some embodiments, a conduit 180 includes a hot bead 182 positioned in the flow path of gas through the conduit 180, for example as shown in FIG. 6. The hot bead 182 can be powered via an electrical connection to the humidifier 102 to maintain the hot bead 182 at a predetermined temperature, for example, about 80° C. In some embodiments, the thermal output of the hot bead 182 is relatively small compared to the quantity of gas passing through the conduit 180 to avoid or limit significant heating of the gas by the hot bead 182.

In use, the power usage of the hot bead 182 is monitored, for example, by a power meter, either relatively close to the hot bead 182 or distant from the hot bead 182, for example, near the power source of the hot bead 182. If the gases within the conduit 180 are stagnant, the power usage of the hot bead 182 is substantially constant. However, if gases are flowing past the hot bead 182, the hot bead 182 will begin to cool as the gas flow carries heat away from the hot bead 182. Additional power will then need to be supplied to maintain the hot bead 182 at the predetermined temperature, resulting in increased power usage by the hot bead 182. A higher gas flow is therefore correlated with increased power usage. Power usage is also related to the temperature and humidity of the gas. A lower temperature gas tends to cool the hot bead 182 at a higher rate than a higher temperature gas. Therefore, power usage increases as gas temperature decreases. A higher humidity gas tends to require a greater amount of energy to heat, thereby producing a greater cooling effect, so power usage increases as humidity increases.

Based on these relationships, it is possible to calculate one of power dissipation, gas flow rate, gas temperature, and gas humidity if measurements of the other three variables are known. This allows humidity to be calculated based on flow rate, temperature, and power dissipation without requiring a stand-alone humidity sensor. To that end, the conduit 180 can also include a temperature sensor 184 and a flow sensor 186. The temperature sensor 184 can be located upstream of the hot bead 182 to help avoid or minimize heating of the gas by the hot bead 182 before temperature is measured. In some embodiments, only a small space separates the temperature sensor 184 and hot bead 182 because a space that is too large can allow the gas temperature to change before reaching the hot bead 182; for example, the gas may cool to a noticeable extent along too long a length of the conduit 180. At the same time, if the space between the temperature sensor 184 and hot bead 182 is too small, the hot bead 182 may inflate the temperature measurement at the temperature sensor 184. An appropriate distance at which to space the temperature sensor 184 and hot bead 182 can be determined by one of skill in the art, depending at least in part on the thermal output of the hot bead 182 and the temperature profile of the gas. The flow sensor 186 can be located near the hot bead 182 to accurately measure the flow of gases passing the hot bead 182. In some embodiments, the hot bead 182 can be located at the chamber outlet. The flow sensor 186 can be located at the chamber inlet.

In some embodiments, two thermistor probes can be positioned on an inlet to the humidification chamber and one or two thermistor probes can be positioned on an outlet from the humidification chamber. Each of these three or four probes can be used to measure gas temperature and also can be heated to a particular temperature for measurement of convective heat loss. The ability to drive these three or four probes in multiple modes allows the possibility to implement various signal processing techniques to increase signal-to-noise ratio and also measure other properties of the gas. For example, through the use of the three or four probes, the humidity added to the gases passing through the humidification chamber 104 can be determined.

Figure 12:
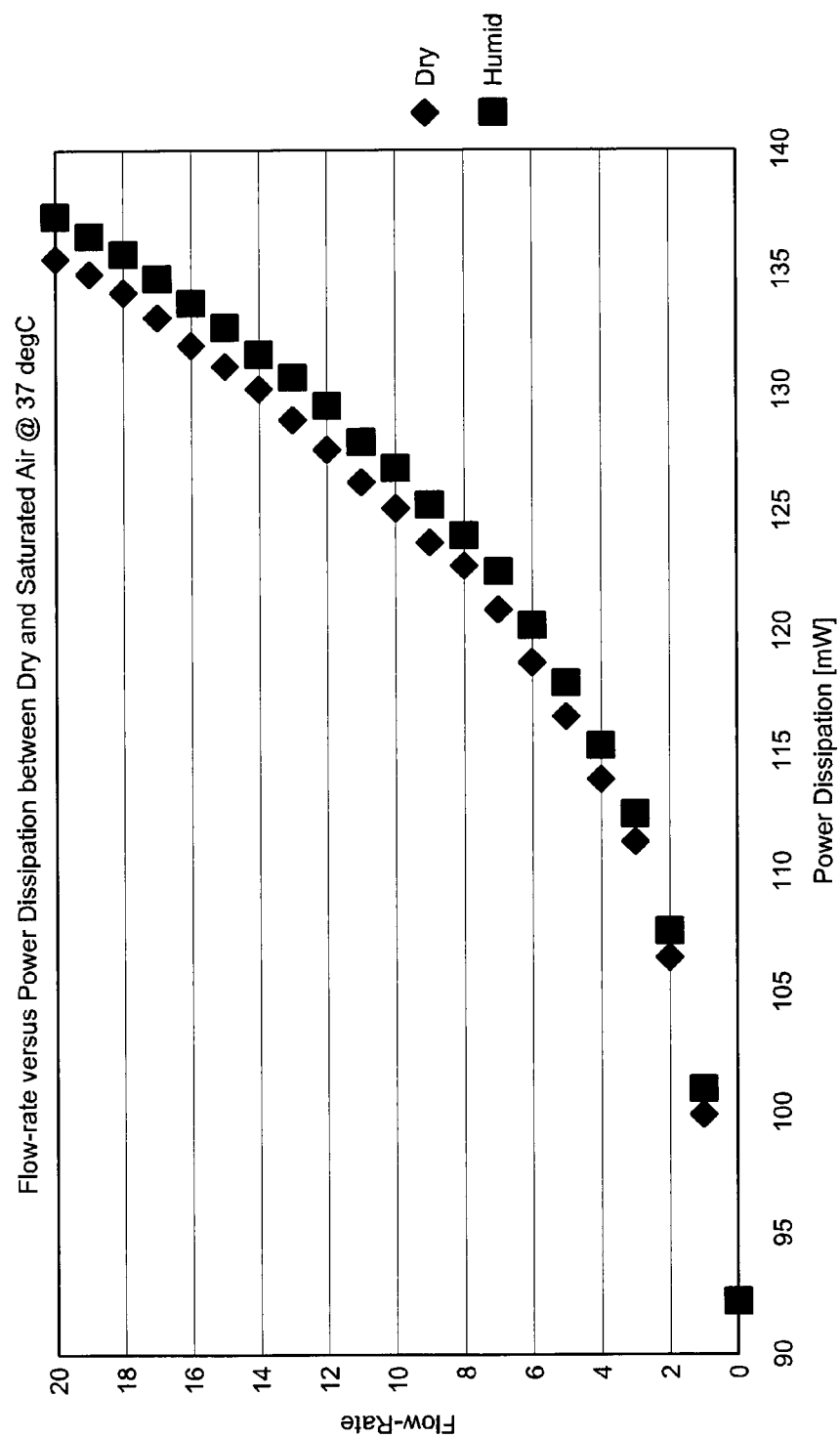
FIG. 12 is a graphical depiction of flow rate versus power dissipation between dry and saturated air at 37 C.

Humid air has been found to increase heat dissipation of heated thermistors. The additional water vapor changes the density, viscosity and more importantly the thermal conductivity will increase the convective heat loss. The different between dry and saturated air at 37° C. and 1 atmosphere will introduce about 12% offset to the flow rate measurement. This shift can be seen graphically in FIG. 12.

Generally, the offset in flow rate measurement on the inlet side of the chamber is undesirable. However, by placing heated probes on both the outlet and the inlet ports to the chamber, the amount of humidity picked up through the chamber can be measured. In some configurations, this measurement can be used to detect water out. In some configurations, either (1) the flow rate measurement on the chamber inlet side is independent of humidity or (2) the amount of humidity present at the inlet port of the chamber is known (e.g., use of a humidity sensor on or near the inlet port). In some embodiments, for example, the temperature sensor 184 and flow sensor 186 provide temperature and flow measurements to the processor 112, which can then determine the humidity of the gas using a formula, look-up table, or the like. The determined humidity can then be used to control one or more other components of the system 100, for example, the temperature of the heater plate 108. In some embodiments, the hot bead 182, temperature sensor 184, and flow sensor 186 can be located in components of the system 100 other than the circuit assembly 123 to allow determination of the humidity at other locations in the system 100. Additionally, in some embodiments, a humidity sensor can replace the hot bead 182, temperature sensor 184, or flow sensor 186 to allow for determination of the power dissipation, temperature, or flow. This can be useful when a power, temperature, or flow sensor is not available or not able to be included in the system 100.

Sensors

Figure 7A:
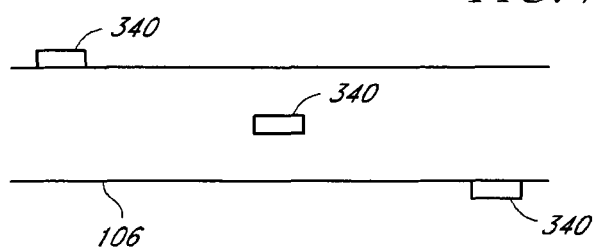
FIGS. 7A-7F illustrate various embodiments of temperature sensing systems.
Figure 7B:
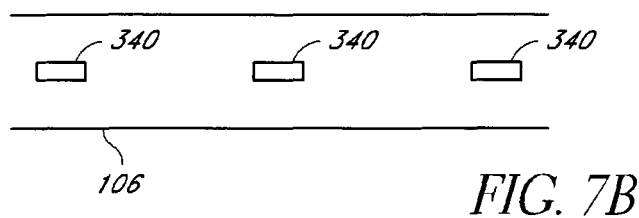
Figure 7C:
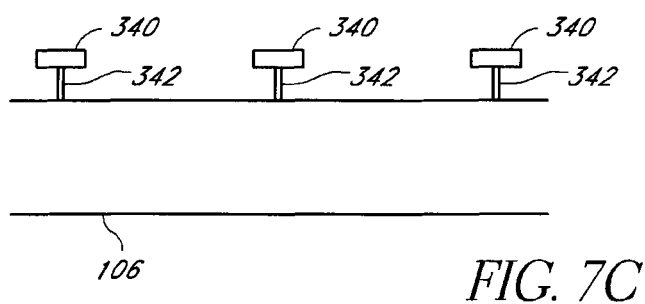

Some environments can be more challenging for optimal functioning of the humidification system 100. In some cases, portions of the circuit assembly 123 may be subject to two or more different temperature environments, and the temperature difference can cause humidified gases to condense in low-temperature sections of the circuit assembly 123 and/or at boundary sections where high-temperature sections meet low-temperature sections. In these situations, as well as in more typical situations in which the entire circuit assembly 123 is generally in substantially the same environment, it can be beneficial to monitor the temperature of the circuit assembly 123 and the ambient temperature surrounding the circuit assembly 123 at various points along the circuit assembly 123. As shown in FIG. 7A, one or more temperature sensors 340 can be arranged around an outer surface of a conduit. As shown in FIG. 7B, the temperature sensors 340 can be arranged substantially in line along a length of a conduit or a portion thereof. Other arrangements are also possible. In some embodiments, one or more of the sensors 340 can be coupled to the conduit via a distance piece 342, which separates the sensor 340 from the conduit. In some cases, this can advantageously provide a more accurate measurement of ambient temperature.

Temperature sensors 340 and/or other sensors described herein can be provided as separate physical devices. However, in some embodiments, one or more sensors can be printed onto the chamber 104 or part of the circuit assembly 123. In some embodiments, the sensors are printed via inkjet printing, for example as described in U.S. Pat. No. 6,406,181, which is hereby incorporated by reference in its entirety. Other methods are also possible. A printed temperature sensor can be formed by printing a pattern of a conductive material onto the desired surface. In some embodiments, a semiconductor (such as silicon) or an organic material can be printed. As the temperature of that surface changes in use, a corresponding change is induced in the resistance of the conductive material. By measuring the resistance, the processor 112 can determine the temperature.

Figure 7D:
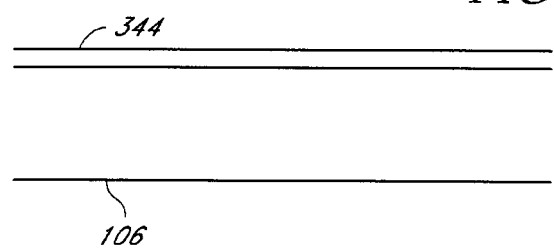
Figure 7E:
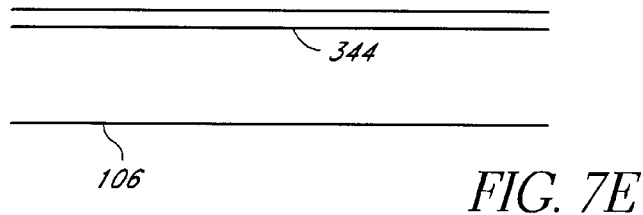

Instead of or in addition to multiple separate temperature sensors 340, the circuit assembly 123 or a portion thereof can include a fiber-optic cable 344 outside the conduit, as shown in FIG. 7D, or within the conduit, as shown in FIG. 7E. Some characteristics of fiber-optic cables, such as Ramen scattering, are dependent on the cable's temperature. By measuring and processing such characteristics, the processor 112 can determine a temperature profile along the cable 344. To measure such a characteristic, an optical pulse is sent along the cable 344, and a monitoring means monitors the back reflection of the pulse. The monitoring means and/or processor 112 can then determine the temperature profile along the cable 344, thereby providing an indication of the temperature of the adjacent conduit. In some embodiments, the cable 344 can be manufactured, preferably extruded, at the same time as the conduit.

Figure 7F:
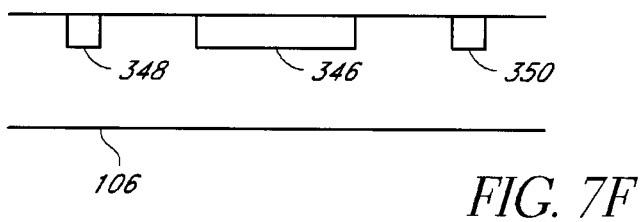

The temperature of the circuit assembly 123 conduits can also be determined via acoustic reflection, such as ultrasonic reflection. As shown in FIG. 7F, a plate 346 is arranged within the conduit. The plate 346, for example, the material comprising the plate 346, is selected so that the plate 346 changes size or another characteristic depending on temperature. In some embodiments, the plate can be fixed on one end and expand freely on the other end. The plate can be in the form of a ring which changes diameter with temperature. A wave producer 348 produces an ultrasonic wave, which travels down the interior of the conduit to a wave receiver 350. The wave receiver can comprise a microphone, a piezo-electric device or the like. As the wave travels through the conduit, the plate 346 interferes with the wave and affects the signal received by the wave receiver 350. The wave receiver 350 then transmits the signal to the processor 112, which can interpret the wave to determine the characteristics of the plate 346 and therefore the temperature of the plate 346. The temperature of the plate 346 is closely related to the temperature of the conduit. In some embodiments, the wave producer 348 and wave receiver 350 can be positioned together or can even be integrated into a single device. In such embodiments, the processor 112 can interpret signals indicative of a reflected portion of the wave received by the receiver 350. In some embodiments, the wave producer 348 produces ultrasonic pulses, the reflections of which are monitored by the wave receiver 350. The speed of sound travelling through the gas will vary depending on the temperature, so it is possible to calculate the temperature based on the time taken for the wave to travel between the wave producer 348 and the wave receiver 350. Further, because the corrugations will tend to change their separation distance depending on the temperature of the tube (that is, closely reflecting the temperature of the gas), it is possible to calculate the temperature of the gas by comparing the measured corrugation separation with a reference corrugation separation. It should be noted that any combination of these methods can also be used.

In some embodiments, components of the system 100 can include one or more water level sensors formed by printing a pattern of conductive material onto a surface. When water contacts the material, the surface capacitance of the material increases. Alternatively or additionally, a surface, such as a hatch bracket, can include multiple conductive tracks of different lengths. Power is applied to the longest track, and voltage, resistance, and/or current are measured on the other tracks. If the measurement exceeds a certain threshold, the processor 112 can infer that liquid is present at a certain level. The processor can similarly determine air humidity by measuring capacitance, as a higher capacitance indicates greater humidity. In some embodiments, components of the system 100 can include a draught sensor in the form of a heater arrangement on a surface. The power dissipation of the heater arrangement can be monitored, and the processor 112 can use the power dissipation to determine flow of ambient air, i.e., whether and to what extent there is a draught.

Patient End Sensor

Typically, humidification systems, such as the system 100 described herein, are adapted for use with a patient having a body temperature within a normal range (for example about, 35° C. to about 39° C.). However, in some cases it may be necessary or desired to use such a system 100 with a patient suffering from hypothermia or hyperthermia, or otherwise where it is desired to alter the patient's core and/or skin temperature. Therefore, in some embodiments, the system 100 can include a temperature sensor located at, adjacent, or near the patient, for example on the patient's skin, to measure the patient's skin temperature and/or core temperature.

In use, when the patient's skin temperature is below a first predetermined level, for example, about 35° C., the system 100 operating parameters can be adjusted so that the temperature of gases at the patient end of the circuit assembly 123 is correspondingly reduced. When the patient's skin is above a second predetermined level, for example, about 39° C., the system 100 operating parameters can be adjusted so that the temperature of gases at the patient end of the circuit assembly 123 is correspondingly increased. Such adjustment of gases temperature can help prevent or reduce the risk of condensate forming in the patient's airway if a large temperature change occurs upon entry into the patient's airway. The patient temperature sensor can provide data to the processor 112, which can then automatically adjust the operating parameters, for example, the heater plate 108 temperature, volume of liquid 232 in the chamber 104, etc. In some embodiments, the processor 112 displays the patient temperature on a display on the humidifier 102, and the user can then decide whether to manually adjust the operating parameters given any other relevant knowledge regarding the patient's medical history and condition. In some embodiments, the patient temperature sensor can itself provide an indication of temperature, for example, via a numerical display, graphical representation, color representation, etc. The user can then similarly decide whether and how to adjust any operating parameters.

Color Changing Indicator

In use, data from various sensors can be provided to the processor 112, which can use the sensor data to adjust the temperature and/or humidity of gas flowing through the system 100 as desired or required by varying the temperature of the heater plate 108. Although the system 100 can include various safety mechanisms and/or processes to inhibit unsafe conditions, such as overheating of one or more components, the user, patient, and/or an electronic device, feedback system, or the like can monitor the temperature, humidity, and/or other conditions of the air within the system 100. In some embodiments, the humidifier 102 can include a display 152. The processor 112 can be configured to cause the display to show the temperature or humidity of the gas at the location of one or more sensors. However, including a display in the humidifier 102 can make the system 100 more bulky, fragile, and/or costly.

As an alternative to a display, one or more components of the system 100 can include a temperature or humidity indicator, for example, a section of a material that changes color depending on varying temperature and/or humidity. An example of such a material is described in U.S. Publication No. 2009/0266145, the entirety of which is hereby incorporated by reference. In use, as gases travel past the temperature or humidity indicator, the temperature or humidity of the indicator will tend to approximate the temperature or humidity of the gases. For example, in one embodiment, the indicator shows a first color, for example, green, when the indicator is below a first predetermined temperature or within a first predetermined range of temperatures and a second color, for example, red, when the indicator temperature exceeds a second predetermined temperature or is within a second predetermined range of temperatures. There may be some degree of lag between a change in temperature or humidity of the gases and a change in temperature or humidity of the indicator. However, the temperature and humidity of the gas typically does not change rapidly, so a potential disadvantage of an indicator lag should not outweigh the advantages of the indicator.

In some embodiments, any one or more components can be made partially or entirely of the indicator material. For example, the Y-piece 124 can be made of the indicator material. In such an embodiment, the specific material is selected to be suitable for the function of the component, for example having sufficient rigidity, moisture resistance, etc., while performing the color-changing indicator function. Alternatively, the indicator material can be overlaid or over-molded onto an existing or conventional component. This can allow for greater flexibility in choosing the indicator material(s) because the indicator material will not necessarily need to be suitable for the function of the component. In such an embodiment, the primary component is at least partially made of a material that is sufficiently thermally conductive to allow transfer of heat from the gases through the component to the indicator material. In another embodiment, a component can include a window of indicator material, i.e., a portion of the component can be removed and replaced with a section of indicator material. In such an embodiment, the component does not need to be made of a thermally conductive material. In some embodiments, the system 100 includes multiple areas of indicator material.

In some embodiments, a camera or the like may be provided in such a position that it monitors one or more color-changing regions. The camera can monitor one or more of part information, water level, flow rate, humidity, temperature, pressure, and/or gas content, particularly oxygen content.

Removing Condensate from Conduit

Although various design features can be used to help control temperature within the circuit assembly 123 to reduce condensation, condensation may be unavoidable in some situations. There is a risk condensate will accumulate in physically low areas of the circuit assembly 123 and possibly lavage the patient and/or occlude the circuit assembly 123. In some embodiments, the system 100 can include a pump having a conduit connected to one or more points along the circuit assembly 123. The pump can be an integral part of the system 100. In use, the pump helps remove condensate from the circuit assembly 123 conduits. In one embodiment, the pump can be connected to the patient conduit 126 proximal to the interface 128 to remove condensate from the patient conduit 126 before the condensate reaches the patient. In some embodiments, the pump can be connected to a physically low point in the circuit assembly 123 to help remove condensate that may accumulate there. The pump can be connected to and deposit collected condensate in humidification chamber 104 or a separate reservoir.

Humidification Chamber Features

Variable Chamber Compressible Volume

Figure 8:
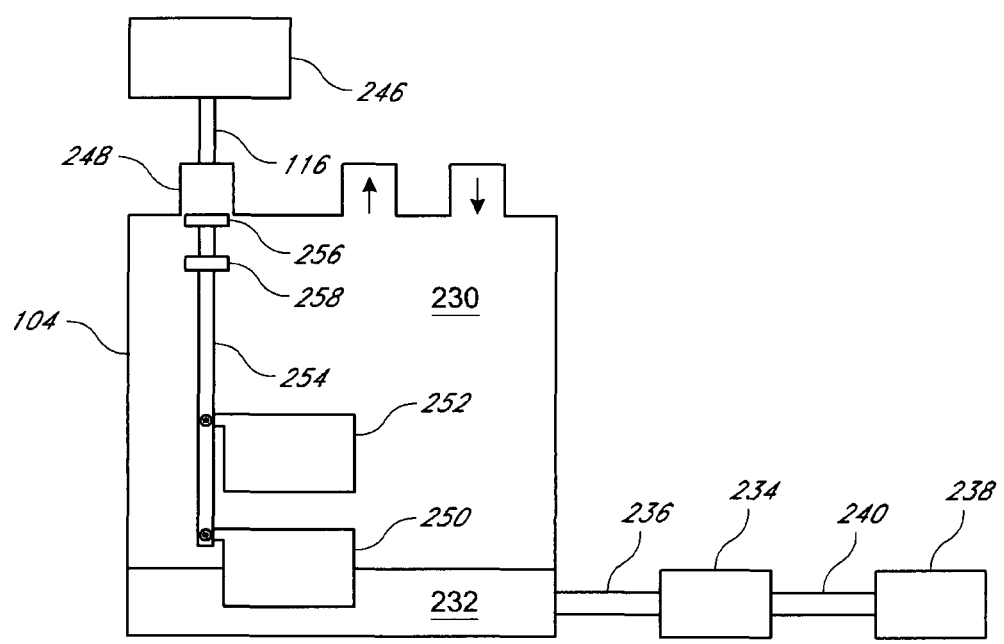
FIG. 8 illustrates an example embodiment of a humidification chamber including a pump and floats.

The humidification chamber 104 generally includes outer walls surrounding an internal cavity 230 as shown in FIG. 8. The chamber 104 walls are typically rigid, making the overall volume of the cavity 230 fixed. The cavity 230 is configured to contain a quantity of liquid 232, often water. The chamber 104 can include a chamber inlet 248 for the connection of a liquid conduit 116 to the chamber 104. Alternatively, the liquid conduit 116 can be integrally formed with or permanently coupled to the chamber inlet 248 and/or chamber 104. The liquid conduit 116 conveys a liquid, for example, water, from a liquid source 246 to the chamber 104. In use, the liquid 232 is heated to form a liquid vapor in the cavity 230. Because the overall cavity 230 volume is fixed and water is a non-compressible fluid, the compressible volume of the cavity 230 is generally constant when the volume of water is constant.

In some embodiments, the system 100 can include a pump 234 that is in fluid communication with the chamber 104 via a pump conduit 236. The pump 234 can remove liquid from the chamber 104, which increases the compressible volume of the cavity 230. The liquid removed from the cavity 230 can be pumped to a reservoir 238 via a reservoir conduit 240. In some embodiments, the liquid removed from the chamber 230 is discarded. A portion of the removed liquid can be stored in the reservoir 238 while the remaining is discarded. In some embodiments, the pump 234 can be used to add liquid to the cavity 230, thereby decreasing the compressible volume of the cavity 230. The liquid added to the cavity 230 can come from the reservoir 238 and/or a liquid source 246. The ability to vary the compressible volume of the cavity 230 in use may advantageously allow the same chamber 104 to be used for various patients where the tidal volume and/or breath frequency of the patient differs. By altering the compressible volume of the cavity 230, the effect on the ventilation waveform can be reduced. For example, systems 100 for use with neonatal patients may be more effective with a reduced compressible volume across the system when compared to an adult patient.

Floats

In some embodiments, humidification chamber 104 can include safety features to help prevent the level of liquid 232 in the cavity 230 from exceeding a particular level. An example embodiment of such a safety feature is a float system as shown in FIG. 8. The chamber 104 can include a first float 250 and, optionally, a second float 252. The first 250 and optional second 252 floats are coupled to a vertically extending piston 254. The piston 254 is oriented to be generally aligned with the chamber inlet 248. The piston 254 includes a first block 256 at or near a top end of the piston 254 and an optional second block 258 near the top end of the piston 254 below the first block 256.

In use, as the liquid level 232 in the chamber 104 rises or falls, the floats 250, 252 rise or fall with the liquid level 232, thereby causing the piston 254 to move up or down as well. When the liquid level 232 in the chamber 104 reaches a first predetermined level, and therefore causes the first float 250 to rise to a first predetermined height within the chamber 230, the piston 254 moves upward causing the first block 256 to occlude the chamber inlet 248. The first block 256 can thereby prevent or slow further ingress of liquid into the cavity 230. When the liquid level 232 in the chamber 104 reaches a second predetermined level, and therefore causes the second float 252 to rise to a second predetermined height within the chamber 230, the piston 254 moves further upward causing the second block 258 to occlude the chamber inlet 248. The first 256 and second 258 blocks can be sized, shaped, and otherwise configured to partially or fully occlude the chamber inlet 248 as desired or required. In some embodiments, the first 256 and second 258 blocks can be different shapes or sizes. For example, the first block 256 can be sized and shaped to only partially occlude the chamber inlet 248 to slow the ingress of liquid into the chamber 104. The second block 258 can be larger than the first block 256 and generally sized and shaped to fully occlude the chamber inlet 248 to prevent any further ingress of liquid into the chamber 104. Other sizes and configurations are also possible.

In some embodiments, one or both of the first 250 and second 252 floats can be coated or made, partially or fully, of a material that allows for the absorption and/or evaporation of liquid, for example water. Thus, the first 250 and/or second 252 float can absorb at least some liquid while sitting in the liquid 232 within the chamber 104.

Alternate Humidifier

Figure 9:
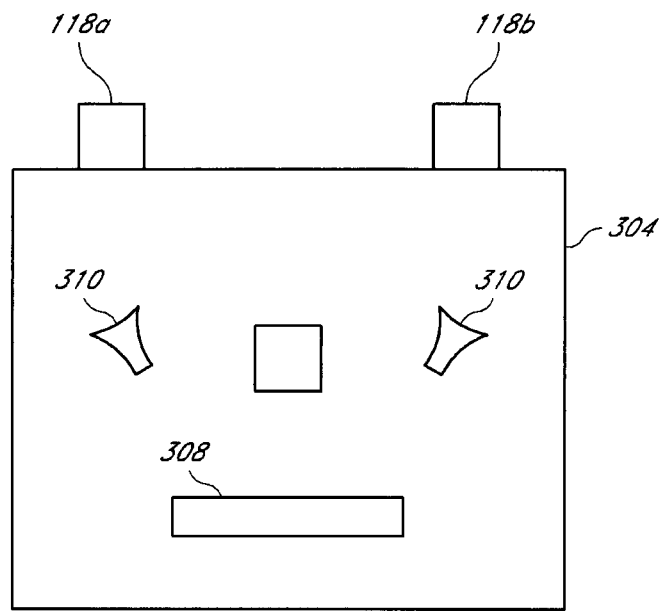
FIG. 9 illustrates an alternative embodiment of a humidification chamber.

The humidification chamber 104 embodiment shown in FIG. 1 is of relatively simple construction, which can allow for reduced manufacturing costs. However, in some situations, it may be beneficial to use an alternative embodiment of a chamber 304, such as illustrated in FIG. 9. The chamber 304 includes a heater plate 308, which can be located near the bottom of the chamber 304. The heater plate 308 can be made of any material suitable for being heated, for example, aluminum, copper, or a suitable plastic as described herein.

In some embodiments, the heater plate 308 is thermally connected to heater plate 108 so that heater plate 308 conducts heat produced by heater plate 108. Alternatively, the heater plate 308 can be independently heated, for example, via a heater wire embedded in the heater plate 308 and powered by an electrical connection to the humidifier 102. If the heater plate 308 is heated independently, heater plate 108 can be omitted. In some embodiments, heater plate 308 can be partially self-heated and partially heated by heater plate 108.

In some embodiments, the chamber 304 can include one or more ejectors 310, which are adapted to eject a controlled quantity of a liquid, for example, water. The ejectors 310 can be similar to ejectors used in inkjet applications, such as those described in U.S. Pat. No. 6,260,959. However, other devices that can eject a controlled quantity of liquid can be used. In use, the heater plate 308 is heated to a temperature sufficient to cause liquid in the chamber 304 to evaporate on contact. Then the ejectors 310 eject the controlled quantity of liquid onto the heater plate 308 and the liquid evaporates. If the liquid used is water, evaporation upon contact with the heater plate 308 will create humidity in the chamber 304. In some embodiments, the quantity of liquid ejected by the ejectors 310 can be varied to control the humidity level within the chamber 304. In some embodiments, the ejectors 310 can cooperate with various sensors as described herein and/or the processor 112 to vary the quantity of liquid ejected and therefore the humidity to a desired level. In an alternative embodiment, the chamber 304 can include a heater at or near a nozzle of each ejector 310. As liquid is ejected from the ejectors 310, the liquid passes the heater, causing the liquid to evaporate. This embodiment can eliminate the need for a heater plate 308.

RFID (Radio Frequency Identification)

Figure 10:
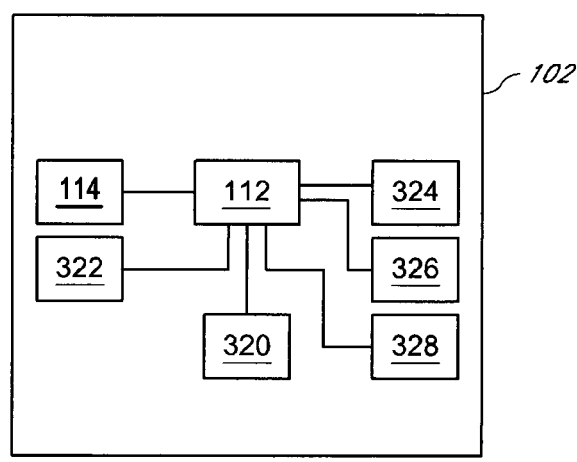
FIG. 10 illustrates an example embodiment of inner components of a heater base.

FIG. 10 illustrates various inner components of an example embodiment of a humidifier 102. In some embodiments, the humidifier 102 includes one or more sensors operatively connected to the processor 112. Additionally or alternatively, the system 100 can include one or more sensors located elsewhere in the system but operatively connected to the processor 112. Some such sensors are described herein. In some embodiments, any or all of the sensors can be operatively connected to a processor remote from the humidifier 102 in addition to or instead of the processor 112. In some embodiments, the processor 112 and/or a remote processor can receive data from a number of different sensors then compile and process the data to determine whether certain error conditions are met. For example, the processor can implement a neural network to determine whether a particular error condition is met based on data from a plurality of distinct sensors.

In some embodiments, the system 100 includes a wireless communication means 320 operatively connected to the processor 112. The wireless communication means 320 can comprise any suitable device or component capable of communicating over a wireless spectrum. Any of all of the sensors and/or a remote processor can be capable of wireless communication as well. The sensor(s) and processor(s) can therefore communicate and transfer data and instructions wirelessly. For example, a sensor located on the interface 128 near the patient could communicate with the processor 112 wirelessly. In some situations, a wired connection between a sensor and processor may be preferred; however, a wireless connection advantageously eliminates the need for a cable.

In some embodiments, a low-distance wireless communication method, for example, Bluetooth or ZigBee, can be used to transmit data between and among sensors and processors. Some or all of the sensors can be configured to propagate the signal among themselves towards a processor. Therefore, information can still be transmitted even when one or more sensors are outside of the ordinary range of the processors.

In some embodiments, sensors and processors 112 from multiple humidification systems 100 can communicate with a single remote monitoring system. This can advantageously allow a user or operator to monitor multiple patients simultaneously and conveniently. In some embodiments, the processor 112 can be adapted to communicate with a network, such as a hospital network. The processor 112 can retrieve information from the network, for example, operational rules. The operational rules can include regulations regarding circuit change frequency, nebulizer use, alarm level, among other things. The can advantageously allow a system 100 to be automatically set up in a particular location associated with a certain network, eliminating or reducing time-consuming manual setup.

In some embodiments, one or more of the wireless sensors can be capable of receiving power from a source other than a wired connection. For example, the sensor(s) can include power generation means such as a thermal energy gathering means, which generates power from thermal energy in warm gas within the conduit (e.g., a Peltier device); a pressure energy gathering means, which generates power from vibrations within the conduit (e.g., a piezoelectric device); and/or a radiation energy gathering means (e.g., a solar panel).

Tilt Sensor

In some embodiments, the humidifier 102 can include a tilt sensor 322 designed to sense a tilt condition of the humidifier. The tilt sensor 322 can include an accelerometer. The tilt sensor 322 may gather data continuously or substantially continuously, or may poll the humidifier condition at regular intervals. A tilt condition can result from a number of situations, such as a sagging or defective bracket upon with the system 100 is mounted, an uneven surface upon with the system is placed, or an incorrect orientation (e.g., as the result of a fall), among other things.

In use, when the tilt sensor 322 senses a tilt condition, the sensor can send an alert signal to the processor 112. Alternatively or additionally, the tilt sensor 322 can send tilt information to the processor 112, and the processor 112 can sense a tilt condition. The processor 112 can then activate any alert means included in the humidification system 100. For example, the system 100 can include an audible alert means 324 for raising an audible alert such as a speaker, bell, and/or siren. In some embodiments, the audible alert means 324 can broadcast a pre-recorded sound and/or message associated with a particular alert, which may be stored in the memory 114. For example, the audible alert means 324 can broadcast a message instructing a user to correct the orientation of the system 100. The system 100 can also or alternatively include a visual alert means 326 for displaying a visual alert, such as a constant light (e.g., an LED), a flashing light, a light of one or more colors associated with an error condition, and/or a screen (e.g., an LCD panel). In some embodiments, the visual alert means 326 can display a pre-determined light arrangement and/or message associated with the particular alert, which can be stored in the memory 114. For example, the visual alert means 326 can display a message instructing the user to correct the orientation of the system 100. In some embodiments, the humidifier 102 can include a remote communication means 328 capable of communicating with a remote computer system and/or remote operator. The remote communication means 328 can produce a remote alert that can instruct a suitable user to correct the orientation of the system 100.

In some embodiments, the humidifier 100 is capable of remedying or minimizing the effect of an incorrect orientation. For example, the system 100 can include orientation means capable of changing the orientation of at least part of the system 100, for example, the humidifier 102 and/or chamber 104. Orientation means can include hydraulic and/or pneumatic legs that can be extended or withdrawn to change the orientation of the system. Parts of the system 100 can be pivotally hinged such that those parts naturally revert to a correct orientation. Other means are possible.

Control Algorithm

In use, the humidification system 100 can be generally controlled by the processor 112, which typically operates according to a program or algorithm stored in the memory 114. The humidifier 102 is often intended for long-term use, while other components of the system, for example, the humidification chamber 104, circuit assembly 123, etc., can be disposable and replaced for each patient and/or periodically for a single patient. Based on the life span of the humidifier 102 and advancements in the field, the program or algorithm stored in the memory 114 may become outdated over time. Updating the memory 114 in conventional ways can require the humidifier to be out of service for a period of time.

Figure 11:
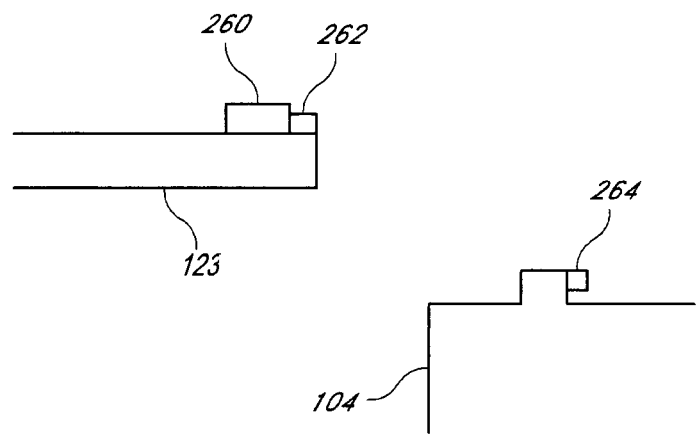
FIG. 11 illustrates means for updating software of a heater base memory.

An improved apparatus and method for updating a memory program or algorithm can include coupling components adapted to store and transfer data to other components of the system 100, such as components frequently replaced, as illustrated in FIG. 11. In some embodiments, the circuit assembly 123 includes a memory 260 suitable for storing data and a first data connection 262 operatively connected to the memory 260. The memory 260 and first data connection 262 can be placed physically adjacent one another and can be connected to an outer wall of the circuit assembly 123. In some embodiments, the memory 260 and first data connection 262 are located near the chamber 104 end of the inspiratory conduit 120. Alternatively, the memory 260 and first data connection 262 can be located at different locations of the circuit assembly 123. The memory 260 and/or first data connection 262 can be removable and/or replaceable. This allows the memory 260 to be replaced with a different memory containing different, possibly updated, software.

A second data connection 264 is coupled to another system component, for example the chamber outlet port 118b, and is configured to operatively connect to the first connection 262. In some embodiments, the first connection 262 can have a male connector and the second connection 264 can have a complementary female connector. Alternatively, the first connection 262 can have a female connector and the second connection 264 can have a complementary male connector. In some embodiments, the first 262 and second 264 connections are mutually couplable. When the first 262 and second 264 connections are coupled, an operative connection is formed between the memory 260 and the processor 112 and/or memory 114 of the humidifier 102.

In some embodiments, an operative connection between the memory 260 and the processor 112 and/or memory 114 of the humidifier 102 can be facilitated by a spine extending from the humidifier 102. The spine can include electrical and data transfer connections and pathways to the processor 112 and/or memory 114. In some embodiments, the first connection 262 operatively connects directly to the spine. Alternatively, the first connection 262 can connect to the second connection 264, which in turn connects to the spine when the humidification chamber 104 is installed on the humidifier 102. In some embodiments, the memory 260 and a connection are coupled to the chamber 104, for example, to the outlet port 118b, and the connection is configured to operatively connect to the spine. Other mechanisms of and locations for connection are also possible.

In some embodiments, the first data connection 262 and second data connection 264 are able to operatively connect without physical contact. For example, one of the connections 262, 264 can include an RFID tag, and the other an RFID interrogator.

In use, upon a successful connection between the first data connection 262, second data connection 264, and/or spine, the processor 112 can compare at least some of the information stored on the memory 260 with information stored on the memory 114 and initiate a data transfer from memory 260 to memory 114 if warranted. For example, the processor 112 can retrieve information regarding the version of software stored on memory 260 and compare that to information regarding the version of software stored on memory 114. If the comparison indicates the memory 260 contains updated software, the processor 112 can initiate the data transfer and copy the software from memory 260 to memory 114. The pre-existing software on memory 114 can be deleted or stored in a non-operative way. The software used for the operation of the humidifier 102, and possibly other components, can therefore be updated without technical expertise or reworking. In some embodiments, the memory 260 can contain simply information regarding the latest version of software available. If a comparison of the version information on the memory 260 with the memory 114 indicates the memory 114 is outdated, the processor 112 can cause a user notification. The user can then take appropriate steps to upgrade the memory 114 if desired. This may allow for notification of outdated software without the expense of including the updated software itself in every conduit. In some embodiments, the updated software may be segmented into a number of separate modules, each of which can be included on different circuit assemblies 123. In use, the processor 112 can gather the modules over time from the attachment of multiple circuit assemblies 123. Once all the modules have been gathered, the updated software can be compiled and the above process can take place.

Display and Feedback

In some embodiments, the humidifier includes a display 152. In some embodiments, the display 152 is an OLED graphical display. In some embodiments, the display 152 is an E ink (electrophoretic ink) display. An E ink display advantageously requires power only to change states, so the display 152 can display information even when powered off. For example, the display 152 can show "Plug Into Power" until power is detected. Humidifiers are sometimes forgotten in busy ICU and other hospital settings as caregivers focus their time and effort into setting up a ventilator, which may be necessary to keep a patient alive, so such a display can advantageously help remind caregivers to set up the humidifier.

Figure 13A:
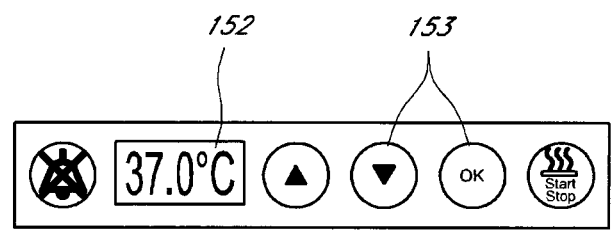
FIG. 13A illustrates an example embodiment of a display and user input buttons for a humidifier.
Figure 13B:
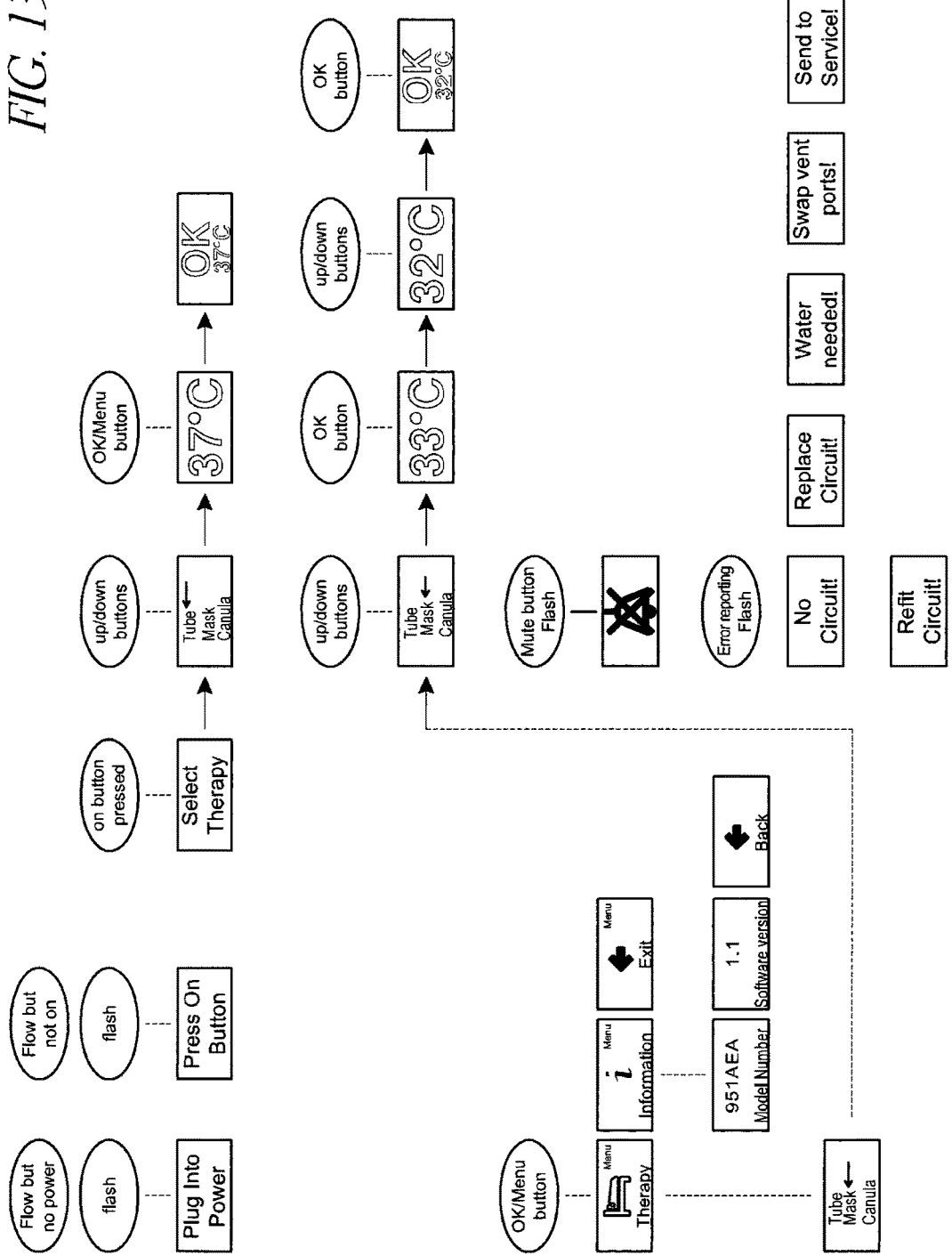
FIG. 13B illustrates example logic and displays for the display of FIG. 13A.

The processor 112 can be configured to cause information, for example, prompts for information, feedback information, etc., to be displayed on the display 152, for example, as shown in FIGS. 13A and 13B. The humidifier can further include mechanisms for user input, for example, power, menu, OK, and up and down arrow buttons 153. Pressing the menu button can cause the processor 112 to cause various options, e.g., types of therapy, temperature and/or humidity settings, etc. to appear on the display 152. The up and down arrow buttons can be used to scroll through various options provided on the display 152. The OK button can be pressed to set, for example, a particular therapy option or level highlighted or selected on the display 152. The menu button can be pressed at any time to view the list of options to change therapy settings. In some embodiments, one button serves as the OK and menu button.

The processor 112 can also be configured to cause various error or warning messages to appear on the display 152, as shown in FIG. 12B. For example, if the humidifier 102 and/or other components of the humidification system are operating on battery power and the battery power drops below a particular threshold, a "Plug into Power" message may flash on the display 152. If gas flow is detected in the humidification system 100 but the humidifier 102 and/or the display 152 is not on, a "Press On Button" message may flash on the display 152. Example error messages can include: "No Circuit" or "Refit Circuit" if the humidification chamber 104 is not installed on the humidifier 102, any electrical connections in the humidification system are not properly made, or sensors as described in greater detail herein are not installed and positioned properly; "Swap Vent Ports" if the inspiratory 120 and/or expiratory 122 conduits are connected incorrectly; "Water Needed" if the liquid source 246, e.g. a water bag, is empty, the liquid conduit 116 from the liquid source 246 to the humidification chamber 104 is not connected properly, there is a kink in the liquid conduit 116, or a valve from the liquid conduit 116 to the humidification chamber 104 is faulty; "Replace Circuit" if a heater wire 138 or a sensor in any of the conduits is faulty; and "Send to Service" if there are internal faults, such as faulty connectors. Other error messages or feedback information can also or alternatively be provided on the display 152.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Furthermore, dimensions of various components provided herein are exemplary, and other dimensions may be used. Thus, it is intended that the scope of the disclosure herein should not be limited by the particular embodiments described above.

What is claimed is:

1. A humidification apparatus comprising:
   a humidification chamber configured to hold a volume of liquid, the chamber comprising:
      a side wall, having a top end and a bottom end, and defining an integrally-formed, uninterrupted side wall between the top end and the bottom end;
      a top wall connected to the top end of the side wall;
      a flat bottom surface connected to and closing the bottom end of the side wall and comprising a heat conductive material, the bottom surface configured to removably contact a flat, heater plate and transfer heat from the heater plate to the volume of liquid in the chamber, wherein the bottom surface separates the volume of liquid from the heater plate in use; and
      an inlet and an outlet extending through at least one of the top wall and the side wall, the chamber having a vertical center plane that divides the chamber into a first side and a second side, the inlet spaced from the vertical center plane and located in the first side and the outlet spaced from the vertical center plane and located in the second side, a gas flow path defined within the humidification chamber between the inlet and the outlet such that the humidification apparatus is a passover humidifier in which a flow of gas along the gas flow path passes over an upper surface of the volume of water;
      a first portion of the side wall or the first portion of the side wall and the top wall being configured to allow for increased heat loss from gases in the gas flow path compared to a second portion of the side wall such that heat loss from the gases in the gas flow path can lower a temperature of the gases prior to entering the outlet thereby enabling a higher operating temperature of the volume of water for enhanced vaporization while the flow of gas provided to the outlet is maintained at a suitable temperature, wherein the first portion comprises a material having a thermal conductivity higher than the second portion, the first portion is positioned in a region of the side wall configured to be above a normal water operating level in use, and the second portion is configured to contact the volume of liquid in use.

2. The humidification apparatus of claim 1, wherein at least a portion of the humidification chamber is configured to vibrate to disturb the volume of liquid within the humidification chamber to inhibit formation of a boundary layer of gases in the flow path adjacent the liquid.

3. The humidification apparatus of claim 1 further comprising a humidifier comprising a housing, a heater plate, and a securing collar, the housing configured to receive the humidification chamber so that the bottom surface of the chamber at least partially contacts the heater plate, the securing collar being configured to secure the humidification chamber in position on the heater plate.

4. The humidification apparatus of claim 3, wherein the housing is configured to extend over the top of at least a portion of the humidification chamber.

5. The humidification apparatus of claim 3, further comprising one or more heating components configured to generally encircle at least a vertically extending portion of the humidification chamber.

6. The humidification apparatus of claim 3, wherein the heater plate is configured to vibrate to disturb the volume of liquid within the humidification chamber to inhibit formation of a boundary layer of gases in the flow path adjacent the liquid.

7. The humidification apparatus of claim 3, wherein the heat conductive material of the bottom surface of the humidification chamber comprises a thermally conductive metal material.

8. The humidification apparatus of claim 7, wherein the thermally conductive metal material comprises a pliable metal foil.

9. The humidification apparatus of claim 3, wherein at least a portion of the side wall of the humidification chamber comprises a thermally conductive metal material.

10. The humidification apparatus of claim 3, wherein the heat conductive material of the bottom surface of the humidification chamber comprises a thermally conductive plastic material.

11. The humidification apparatus of claim 3, wherein at least a portion of the side wall of the humidification chamber comprises a thermally conductive plastic material.

12. The humidification apparatus of claim 3, wherein the heater plate comprises one or more holes.

13. The humidification apparatus of claim 3, further comprising thermally conductive inserts that extend through the bottom surface of the humidification chamber into the humidification chamber.

14. The humidification apparatus of claim 1, wherein the bottom surface of the humidification chamber and the heater plate are planar.

15. The humidification apparatus of claim 1, wherein the gas flow path extends across a surface of the volume of liquid.

16. A humidification apparatus comprising:
a humidification chamber configured to hold a volume of liquid, the chamber comprising:
a side wall;
a top wall connected to the side wall;
a bottom surface connected to the side wall and comprising a heat conductive material, the bottom surface configured to removably contact a heater plate and transfer heat from the heater plate to the volume of liquid in the chamber, wherein the bottom surface separates the volume of liquid from the heater plate in use; and
an inlet and an outlet extending through at least one of the top wall and the side wall, the chamber having a vertical center plane that divides the chamber into a first side and a second side, the inlet spaced from the vertical center plane and located in the first side and the outlet spaced from the vertical center plane and located in the second side, a gas flow path defined within the humidification chamber between the inlet and the outlet such that the humidification apparatus is a passover humidifier in which a flow of gas along the gas flow path passes over an upper surface of the volume of water;
a first portion of the side wall or the first portion of the side wall and the top wall being configured to allow for increased heat loss from gases in the gas flow path compared to a second portion of the side wall such that heat loss from the gases in the gas flow path can lower a temperature of the, wherein the first portion comprises a material having a thermal conductivity higher than the second portion, the first portion is positioned in a region of the side wall configured to be above a normal water operating level in use, and the second portion is configured to contact the volume of liquid in use.

17. The humidification apparatus of claim 16, wherein at least a portion of the humidification chamber is configured to vibrate to disturb the volume of liquid within the humidification chamber to inhibit formation of a boundary layer of gases in the flow path adjacent the liquid.

18. The humidification apparatus of claim 16, further comprising a humidifier comprising a housing, a heater plate, and a securing collar, the housing configured to receive the humidification chamber so that the bottom surface of the chamber at least partially contacts the heater plate, the securing collar being configured to secure the humidification chamber in position on the heater plate.

19. The humidification apparatus of claim 18, wherein the housing is configured to extend over the top of at least a portion of the humidification chamber.

20. The humidification apparatus of claim 18, further comprising one or more heating components configured to generally encircle at least a vertically extending portion of the humidification chamber.

21. The humidification apparatus of claim 16, wherein the heat conductive material of the bottom surface of the humidification chamber comprises a thermally conductive metal material.

22. The humidification apparatus of claim 21, wherein the thermally conductive metal material comprises a pliable metal foil.

23. The humidification apparatus of claim 16, wherein at least a portion of the side wall of the humidification chamber comprises a thermally conductive metal material.

24. The humidification apparatus of claim 16, wherein at least a portion of the bottom surface of the humidification chamber comprises a thermally conductive plastic material.

25. The humidification apparatus of claim 16, wherein the heat conductive material of the bottom surface of the humidification chamber comprises a thermally conductive plastic material.

26. The humidification apparatus of claim 16, further comprising thermally conductive inserts that extend through the bottom surface of the humidification chamber into the humidification chamber.

27. The humidification apparatus of claim 16, wherein the bottom surface of the humidification chamber is planar.

* * * * *

UNITED STATES PATENT AND TRADEMARK OFFICE
CERTIFICATE OF CORRECTION

PATENT NO. : 10,449,323 B2  
APPLICATION NO. : 14/389331  
DATED : October 22, 2019  
INVENTOR(S) : Dexter Chi Lun Cheung et al.

Page 1 of 1

It is certified that error appears in the above-identified patent and that said Letters Patent is hereby corrected as shown below:

In the Specification

In Column 5, Line 11 (approx.), delete "ore" and insert --or--.

In Column 7, Line 44, delete "memory." and insert --memory;--.

In Column 20, Line 30, delete "about," and insert --about--.

Signed and Sealed this  
Twenty-fifth Day of February, 2020

Andrei Iancu  
*Director of the United States Patent and Trademark Office*